(12) United States Patent
Laezza et al.

(10) Patent No.: US 12,291,553 B2
(45) Date of Patent: May 6, 2025

(54) NON-OPIOID ANTI-PAIN MEDICATION

(71) Applicant: The Board of Regents of The University of Texas System, Austin, TX (US)

(72) Inventors: Fernanda Laezza, Galveston, TX (US); Jia Zhou, Galveston, TX (US); Jin Mo Chung, Galveston, TX (US); Pingyuan Wang, Galveston, TX (US); Jun-Ho La, Galveston, TX (US); Oluwarotimi Folorunso, Galveston, TX (US); Aditya Singh, Galveston, TX (US)

( * ) Notice: Subject to any disclaimer, the term of this patent is extended or adjusted under 35 U.S.C. 154(b) by 609 days.

(21) Appl. No.: 17/425,688

(22) PCT Filed: Jan. 24, 2020

(86) PCT No.: PCT/US2020/015079
§ 371 (c)(1),
(2) Date: Jul. 23, 2021

(87) PCT Pub. No.: WO2020/154679
PCT Pub. Date: Jul. 30, 2020

(65) Prior Publication Data
US 2022/0185855 A1    Jun. 16, 2022

Related U.S. Application Data

(60) Provisional application No. 62/796,916, filed on Jul. 23, 2021.

(51) Int. Cl.
*C07K 14/50* (2006.01)
*A61K 38/00* (2006.01)
*A61P 25/04* (2006.01)
*C07K 5/117* (2006.01)

(52) U.S. Cl.
CPC .............. *C07K 14/50* (2013.01); *A61P 25/04* (2018.01); *C07K 5/1024* (2013.01); *A61K 38/00* (2013.01)

(58) Field of Classification Search
CPC ....... C07K 14/50; C07K 5/1024; A61P 25/04; A61K 38/00
See application file for complete search history.

(56) References Cited

PUBLICATIONS

Ali et al, Modulation of the FGF14:FGF14 homodimer interaction through short peptide fragments, CNS Neurol Disord Drug Targets, 2014, 13, pp. 1559-1570, Author manuscript enclosed pp. 1-22.*

* cited by examiner

*Primary Examiner* — Li N Komatsu
(74) *Attorney, Agent, or Firm* — HYLTON-RODIC LAW PLLC

(57) ABSTRACT

The present invention relates to novel small molecules Formula I and pharmaceutically acceptable salts thereof as well as the preparation and the use thereof to inhibit FGF13-1b.

Formula I

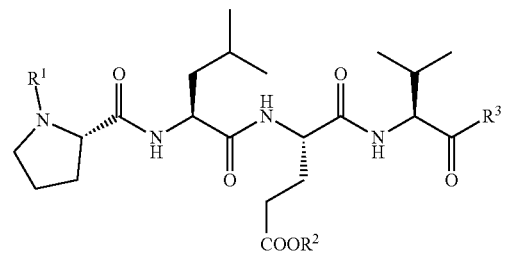

19 Claims, 12 Drawing Sheets
(11 of 12 Drawing Sheet(s) Filed in Color)

FIG. 11

*In Vitro* DMPK Profile of PW164

| Compounds | PW164 | |
|---|---|---|
| Dose | PO (20 mg/kg) | IV (10 mg/kg) |
| $t_{1/2}$ (h) | 1.08 ± 0.05 | 0.17 ± 0.02 |
| $C_{max}$ (ng/mL) | 364.0 ± 166.3 | 2059.1 ± 321.1 |
| $AUC_{0-t}$ (ng·h/mL) | 225.4 ± 43.4 | 634.5 ± 52.4 |
| $V_{ss}$ (L/kg) | 133.07 ± 18.31 | 3.8 ± 0.71 |
| CL (mL/min/kg) | 86.11 ± 14.57 | 15.64 ± 1.15 |
| F (%) | 17.76 ± 3.42 | NA |

| Blood-Brain Barrier (BBB) Studies | |
|---|---|
| Brain/Plasma Ratio | NA |

FIG. 12

*In Vitro* DMPK Profile of PW164

| Compounds | | PW164 |
|---|---|---|
| Microsomal Metabolic Stability | Clearance (μL/min/mg) | 1064.7 (Human) |
| | | 984.2 (Mouse) |
| | $T_{1/2}$ in plasma(min) | 1.3 |
| | | 1.4 |
| Plasma Metabolic Stability | $T_{1/2}$ in plasma(min) | 1126.8 (Human) |
| | | 9.4 (Mouse) |
| Plasma Protein Binding (unbound%) | | 1.6 (Human) |
| | | NA |
| Whole Blood Stability | $T_{1/2}$ (Min) | 43.2 (Human) |
| | | NA (Mouse) |
| Permeability (Efflux ratio; Classification) | | 55.2 (without Pgp inhibitor) / low |
| | | 0.7 (with Pgp inhibitor) |
| Pgp substrate | | Yes |
| hERG ($IC_{50}$, μM) | | > 30 |
| CYP450 inhibition (%, @10μM) | | CYP3A4(MDZ): 75.5 ± 0.3 |
| | | CYP3A4(Testo): 24.5 ± 8.9 |
| | | CYP1A2: 11.8 ± 3.2 |
| | | CYP2C9: 4.7 ± 0.5 |
| | | CYP2D6: 14.8 ± 8.8 |
| | | CYP2C19: 1.2 ± 1.4 |
| | | CYP2C8: 38.5 ± 9.2 |
| | | CYP2B6: 23.5 ± 12.7 |

NON-OPIOID ANTI-PAIN MEDICATION

CROSS REFERENCE TO RELATED APPLICATIONS

This application is a U.S. national stage application of International Application No. PCT/US20/15079, filed 2020 Jan. 24, which claims the benefit of the filing date of U.S. Provisional Appl. No. 62/796,916, filed 2019 Jan. 25, the contents of which are hereby incorporated by reference in their entirety.

STATEMENT OF FEDERALLY SPONSORED RESEARCH AND DEVELOPMENT

This invention was made with government support under the NIH Grant No. R01 MH111107 awarded by the National Institutes of Health (NIH). The government has certain rights in the invention.

FIELD OF THE INVENTION

The field of the invention relates generally to novel small molecule inhibitors of fibroblast growth factor 13 (FGF13-1a and FGF13-1b) as well as the preparation and the use thereof.

BACKGROUND

Opioid-use disorder (OUD) is a national public health emergency in the United States. Official reports indicate over 115 deaths per day from opioid addiction with an estimated total economic burden of $78.5 billion a year. As the primary source of opioid addiction is ascribed to misuse of current pain medications, efforts to combat the opioid epidemic should focus on novel, non-addictive, safe medications to manage chronic inflammatory and post-operative pain.

Pain is most commonly initiated by firing of peripheral sensory neurons that transduce painful stimulation into electrical signals through activity of voltage-gated Na+ (Nav) channels.

The opioid crisis has been officially declared a nationwide Public Health Emergency <https://www.whitehouse.gov/opioids> and initiatives such as HEAL (Helping to End Addiction Long-term; <https://www.nih.gov/heal-initiative>) have been created to accelerate scientific solutions to stem the national opioid epidemic. Because OUD develops primarily as a consequence of misuse of opioid-based painkillers, the first step toward ending OUD is to develop new non-opioid pain medications.

The need of new biological targets for pain medication. The biological cause of peripheral pain is the persistent firing of dorsal root ganglia (DRG) neurons triggered by nociceptive stimulation. The ultimate goal of pain medications is to suppress persistent nociceptive firing without peripheral or central side effects. None of the current medications (based on opioids or local anesthetics) meet these criteria. Opioids-based medications, which cause indirect suppression of firing through u-opioid receptor signaling, have major abuse liability. Local anesthetics cause indiscriminate numbness by blocking normal sensory function with life threating risks that make them impractical for unsupervised use. To tackle pain at its root cause we need a paradigm shift in drug discovery with medications based on druggable targets restricted to pain mechanisms.

The FGF13: Nav1.6 channel complex: a new target for pain medication development. In both normal and pain related conditions DRG neuron firing depends upon activation of the pore-forming alpha subunit of the voltage-gated Na+ channel. However, evidence indicates that protein: protein interactions (PPI) between alpha and accessory subunits of the Nav channel confers specificity to pain related firing. Studies have established the two isoforms of the FGF13 accessory subunit of Nav1.6 as functional determinants of nociceptive firing through PPI with the intracellular C-terminal tail of Nav1.6, FGF13-1a and 1b control channel gating, biophysical properties and cellular targeting in an isoform-specific manner. Due to biological variations in the two isoforms' mechanism of action, Nav1.6 channel pools containing FGF13-1b are more prone to conduct persistent Na+ currents (known as "resurgent" current) than FGF13-1a, leading to aberrant nociceptive firing of DRG fibers. In neuroinflammatory pain models, the relative contribution of FGF13 isoforms is dominated by FGF13-1b: Nav1.6 complexes and 10-20-mer peptides that mimic FGF13-1a effectively reverse maladaptive firing of DRG associated with pain. This evidence inspired our drug design strategy to create compounds that inhibit FGF13-1b and mimic FGF13-1a (FIG. 1). Additionally, recent studies have provided evidence for FGF13 as a regulator of Nav1.7, another Nav channel isoform expressed in DRG neurons and involved in a variety of pain mechanisms, including neuroinflammatory pain. Given structural and sequence similarity between the two channel isoforms, compounds that target the FGF13: Nav1.6 channel interface might interfere with the closely related FGF13: Nav1.7 channel complex.

The inventors discovered certain compounds, as exemplified by PW164, which inhibit FGF13-1b and acts as a FGF13-1a mimetic. Strikingly, unlike common local anesthetics, PW164 does not affect normal sensory function, but rather acts exclusively on pain-induced transmission.

Compound PW164 was synthesized and validated in cell assays against PPIs reconstituted in the physiological environment (FIG. 2,3) and electrophysiology assays (FIG. 5,6) that were complemented by in vivo preclinical animal models of pain (FIG. 8-10). With unique mixed positive (PAM) and negative (NAM) allosteric modulation properties, PW164 acts as an FGF13-1b inhibitor (FIG. 6), and as an FGF13-1a mimic (FIG. 5), by a mechanism of action consistent with reduction of channel availability (NAM) and potentiation of Na+ transient currents (PAM). In preclinical studies, PW164 effectively reduces capsaicin-induced (FIG. 11, 12) and post-operative pain (FIG. 10) with a single-injection efficacy that exceeds the efficacy of the local anesthetic bupivacaine. Furthermore, unlike bupivacaine, PW164 inhibits pain, but has no effects on normal sensory function (FIG. 9), making this compound an ideal candidate for targeted pain medication development with limited side effects.

This background information is provided for the purpose of making information believed by the applicant to be of possible relevance to the present invention. No admission is necessarily intended, nor should it be construed, that any of the preceding information constitutes prior art against the present invention.

SUMMARY

The inventors have surprisingly discovered novel non-opioid compounds with anti-hyperalgesic properties in behavioral models of inflammatory and post-operative pain. The inventors also surprisingly discovered that unlike common local anesthetics, the invention as exemplified by PW164, does not affect normal sensory function, but rather acts exclusively on pain-induced transmission.

One aspect of the invention pertains to compounds of Formula I or pharmaceutically acceptable salts thereof, wherein:

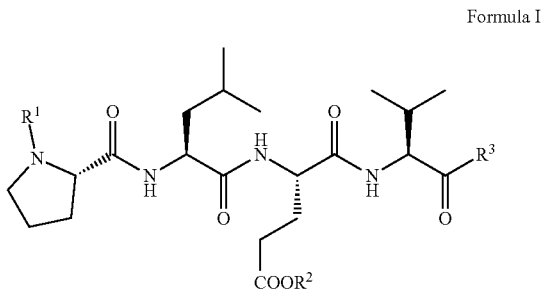

Formula I $R^1$ is H, alkyl, cycloalkyl, aryl, heteroaryl, $R^4CO$—, $R^5NHCO$—, $R^6OCO$—, $R^7SO_2$—, or Fmoc; where $R^4$, $R^5$, $R^6$ and $R^7$ are independently selected from the group consisting of alkyl, cycloalkyl, alkenyl, aryl, heteroaryl, adamantyl, and benzyl, wherein $R^4$, $R^5$, $R^6$ and $R^7$ is optionally substituted with one or more chosen substituents chosen from —OH, —CN, —$NH_2$, and halogen;

$R^2$ is H, alkyl, aryl, heteroaryl, cycloalkyl, or Boc;

$R^3$ is OH, alkoxy, allyloxy, —$NR^8R^9$; wherein $R^8$ and $R^9$ are independently selected from the group consisting of H, alkyl, aryl, and heteroaryl; or $R^8$ and $R^9$ are optionally joined to form a N-containing heterocycle with 1-3 heteroatoms; and wherein $R^1$ and $R^2$ are not both hydrogen.

It is to be understood that both the foregoing general description of the invention and the following detailed description are exemplary, and thus do not restrict the scope of the invention.

BRIEF DESCRIPTION OF THE FIGURES

The patent or application file contains at least one drawing/photograph executed in color. Copies of this patent or patent application publication with color drawing(s) will be provided by the Office upon request and payment of the necessary fee.

Schemes illustrate the experimental design testing the effect of local and intrathecal PW164 on normal mechanical sensitivity (left) and capsaicin-induced mechanical hypersensitivity (right), respectively. A. Unlike the local anesthetic bupivacaine (Bup; n=5) that causes complete sensory block, intraplantar injection of PW164 (n=3) preserves normal mechanical sensation intact, showing no changes in paw withdrawal response to LVF and HVF stimulations. B. Intrathecal PW164 (n=3) does not inhibit capsaicin-induced mechanical hypersensitivity. Drugs were given at the indicated concentrations in a final injected volume of 3 ul (A) or 5 ul (B); in panel B, drugs were injected 30 min after Cap injection.

Figure 10:
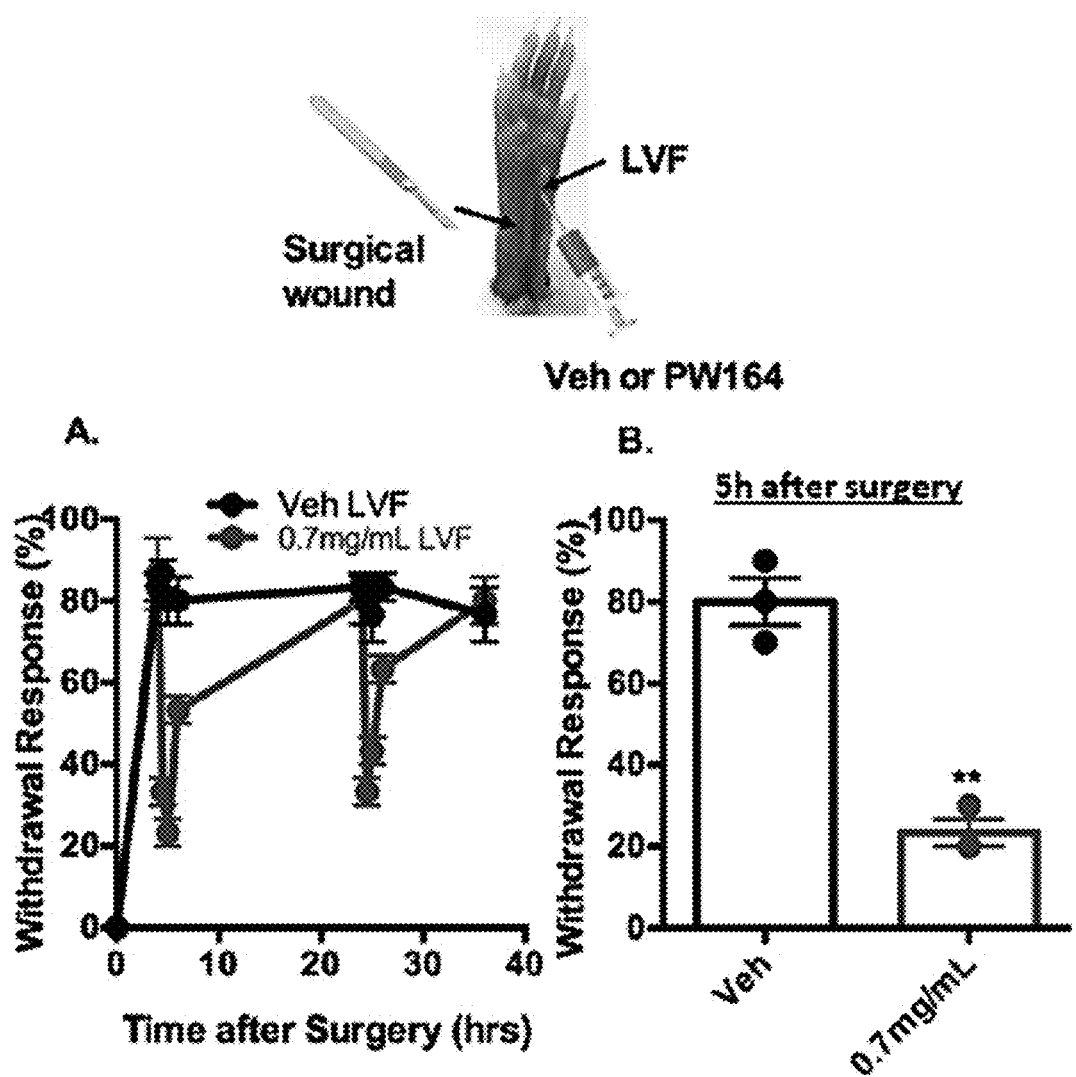

FIG. 10. PW164 administered at the surgical wound inhibits mechanical hypersensitivity in the plantar incision model. After plantar incision, mice develop profound mechanical hypersensitivity to LVF at the surgical wound (scheme). When administered to the wound, PW164 inhibits the hypersensitivity. PW164 was given at the indicated concentrations in a final injected volume of 3 μL; data are represented as mean±SEM; N=3 for each group and time point. **p<0.01; Student's t-test.

FIG. 11. In vitro DMPK profile of PW164 (an exemplary embodiment of the invention) delivered either orally (20 mg/kg) or intravenously (10 mg/kg). Relevant parameters such as half-time (t1/2), maximal concentration (Cmax), area under the curve (AUC), apparent volume of distribution at steady state (Vss), clearance (CL) and bioavailability (% F) were calculated in a mouse model. In addition, brain/plasma ratio studies reveals that PW164 cannot permeate into the brain, making abuse liability of this compound very unlikely.

FIG. 12. In vitro studies of PW164 plasma and blood metabolic stability in rodent and preclinical human models. Intestinal absorption using the P-glycoprotein (P-gp) inhibition ($IC_{50}$) assay as well as activity against the human cardiac ERG channel (hERG) as well as liver toxicity tests against various isoforms of the cytochrome P450 were conducted. These DMKP studies (see e.g., FIGS. 11 and 12) reveals at least that:

(a) PW164 has moderate oral bioavailability and moderate oral half-life. PW164 has no hERG and CYP450s liabilities. PW164 has high human plasma metabolic stability and human whole blood stability; and
(b) PW164 cannot penetrate BBB. This might be favorable for peripheral therapeutics with the advantage of no brain-associated side toxicity effects.

DETAILED DESCRIPTION 1.0. Definitions 1.0. Definitions

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977), which is incorporated herein by reference in its entirety, for further examples of pharmaceutically acceptable salt).

The term "HBTU" refers to 3-[Bis(dimethylamino)methyliumyl]-3H-benzotriazol-1-oxide hexafluorophosphate (also known as 2-(1H-benzotriazol-1-yl)-1,1,3,3-tetramethyluronium hexafluorophosphate).

The term "HOBt" refers the following structure, known as 1-hydroxybenzotriazole, (including hydrates and polymorphs, thereof):

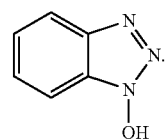

The term "DIEA" refers to N,N-Diisopropylethylamine (also known as Hünig's base, DIPEA, and ethyldiisopropylamine).

The term "DCM" refers to dichloromethane (also known as methylene chloride).

The term "EDCI" refers to 1-Ethyl-3-(3-dimethylaminopropyl) carbodiimide (EDC, EDAC or EDCI).

The term "TFA" refers to trifluoroacetic acid.

The term "rt" refers to room temperature.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl", by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include —$(CH_2)_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —$NH_2$ group.

An "amido" group refers to an —$CONH_2$ group. An alkylamido group refers to an —CONHR group wherein R is as defined above. A dialkylamido group refers to an —CONRR' group wherein R and R' are as defined above.

The term "halogen" or "halo" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1~4 carbons.

A "thio" group refers to an —SH group.

An "alkylthio" group refers to an —SR group wherein R is alkyl as defined above.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "arylamine" or "arylamino" as used herein by itself or as part of another group refers to an amino group which is substituted with an aryl group, as defined above.

As used herein, the term "arylalkyl" denotes an alkyl group substituted with an aryl group, for example, Ph-$CH_2$- etc.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl (—$C(O)NR^2$), unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —$NH_2$, —NH($C_{1-4}$alkyl), —N($C_{1-4}$alkyl)$_2$, —NO2, —S($C_{1-4}$alkyl), —$SO_2$($C_{1-4}$alkyl), —$CO_2$($C_{1-4}$alkyl), and —O($C_{1-4}$alkyl).

PW0164 is used throughout this description interchangeably with PW164 to refer to:

PW0164

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/prevented, but has been deemed by a physician, clinician or other medical professional to be at risk for developing said disorder, disease or condition.

The terms "treating," "treatment" and the like as used herein includes the management and care of a subject (preferably a mammal, more preferably a human) for the purpose of combating a disease, condition, or disorder and includes the administration of a compound of the present disclosure to prevent the onset of the symptoms or complications, alleviate the symptoms or complications, or eliminate the disease, condition, or disorder.

It is to be understood that both the foregoing descriptions are exemplary, and thus do not restrict the scope of the invention.

2.0. Compounds

The present invention provides a compound of the Formula I and pharmaceutically acceptable salts thereof, wherein:

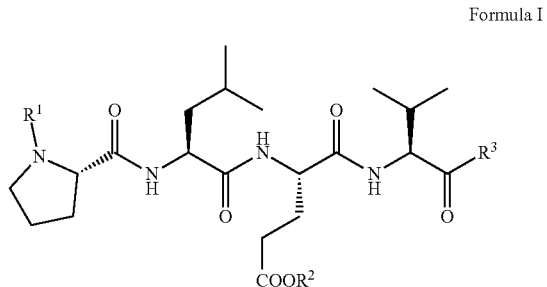

Formula I $R^1$ is H, alkyl, cycloalkyl, aryl, heteroaryl, $R^4CO$—, $R^5NHCO$—, $R^6OCO$—, $R^7SO_2$—, or Fmoc-;

where $R^4$, $R^5$, $R^6$ and $R^7$ are independently selected from the group consisting of alkyl, cycloalkyl, alkenyl, aryl, heteroaryl, adamantyl, and benzyl, wherein $R^4$, $R^5$, $R^6$ and $R^7$ is optionally substituted with one or more chosen substituents chosen from —OH, —CN, —NH$_2$, and halogen;

$R^2$ is H, alkyl, aryl, heteroaryl, cycloalkyl, or Boc;

$R^3$ is OH, alkoxy, allyloxy, —NR$^8$R$^9$; wherein $R^8$ and $R^9$ are independently selected from the group consisting of H, alkyl, aryl, and heteroaryl; or $R^8$ and $R^9$ are optionally joined to form a N-containing heterocycle with 1-3 heteroatoms; and wherein $R^1$ and $R^2$ are not both hydrogen.

In some embodiments of Formula I and pharmaceutically acceptable salts thereof, $R^1$ is H.

In some embodiments of Formula I and pharmaceutically acceptable salts thereof, $R^1$ is $R^4CO$— and $R^4$ is alkyl, cycloalkyl, alkenyl, aryl, or Fmoc.

In some embodiments of Formula I and pharmaceutically acceptable salts thereof, $R^1$ is $R^5NHCO$— and $R^5$ is adamantyl.

In some embodiments of Formula I and pharmaceutically acceptable salts thereof, $R^1$ is $R^6OCO$— and $R^6$ is benzyl or substituted benzyl.

In some embodiments of Formula I and pharmaceutically acceptable salts thereof, wherein $R^1$ is $R^7SO_2$— and $R^7$ is 4-fluorophenyl.

In some embodiments of Formula I and pharmaceutically acceptable salts thereof, $R^2$ is Boc.

In some embodiments of Formula I and pharmaceutically acceptable salts thereof, $R^3$ is OH, —OMe, or allyloxy.

In some embodiments of Formula I and pharmaceutically acceptable salts thereof, $R^3$ is —NR$^8$R$^9$ and $R^8$ and $R^9$ is chosen from H and any of the following substituents:

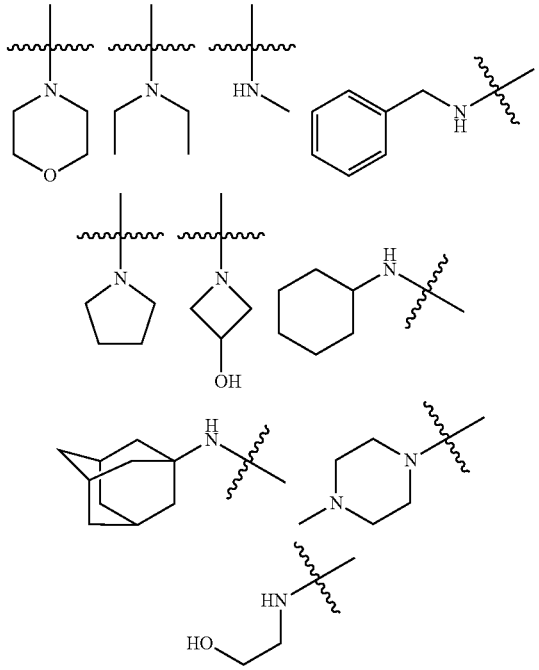

In some embodiments, Formula I is chosen from:

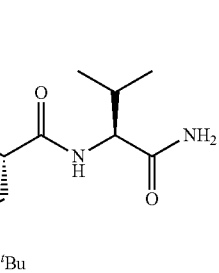

-continued
PW0184
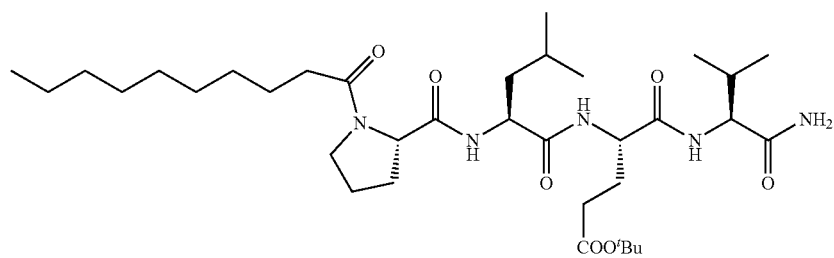
PW0169
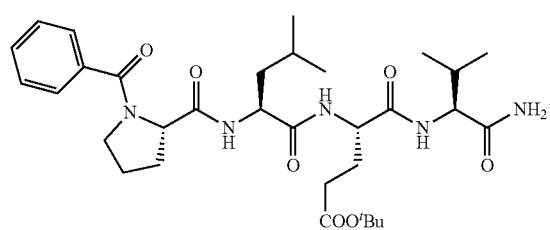
PW0183
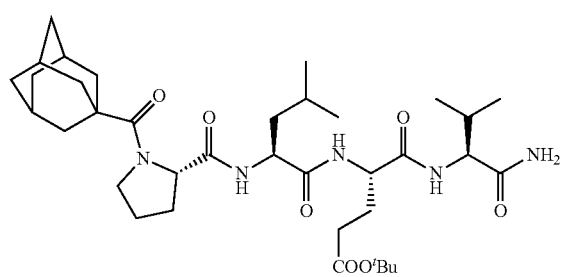
PW0185
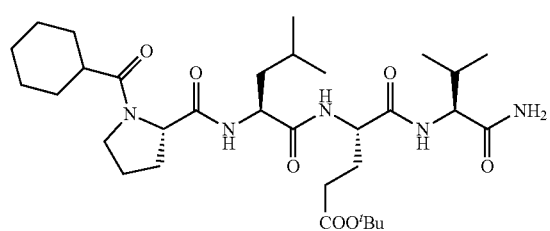
PW0192
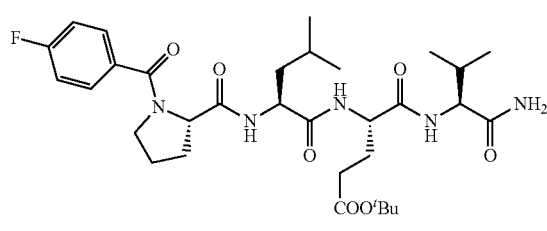
PW0173
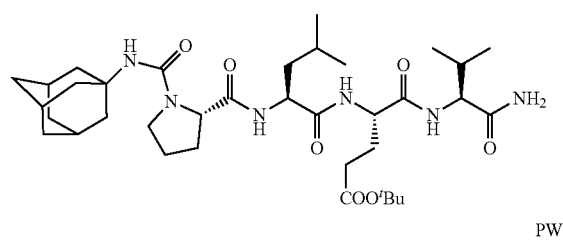
PW161
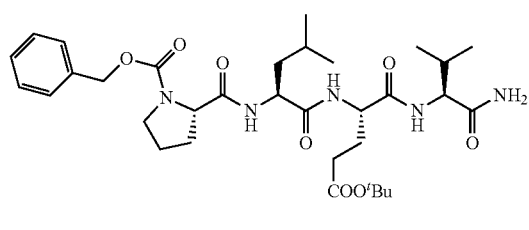
PW0164
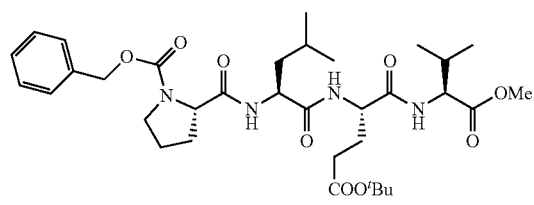
PW0197
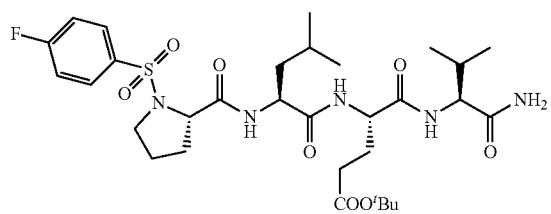
PW0564
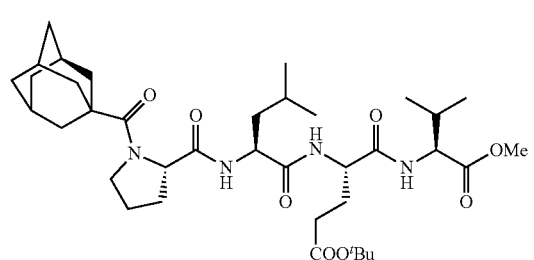
PW0565
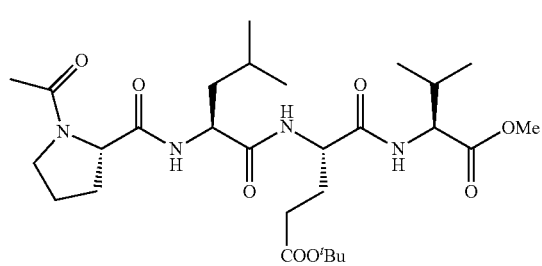

-continued
PW0576
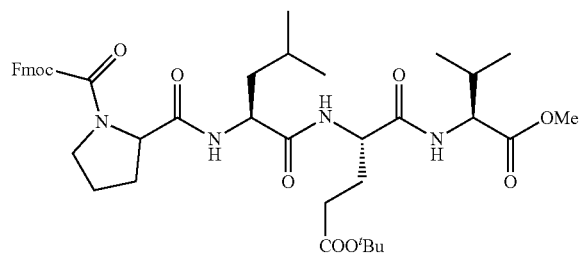
PW0531
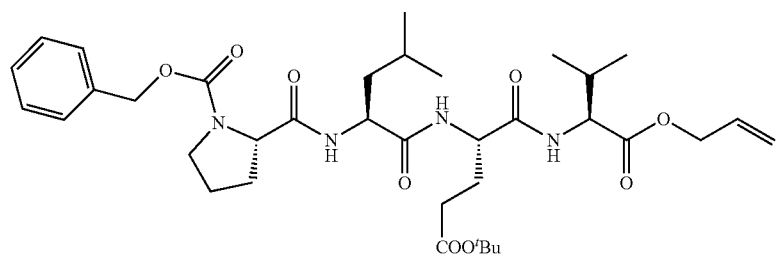
PW0533
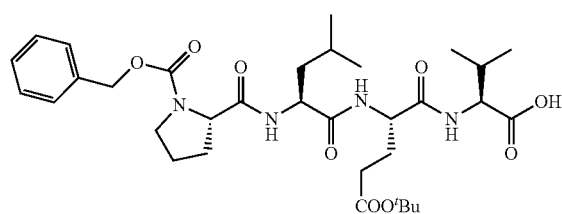
PW0536
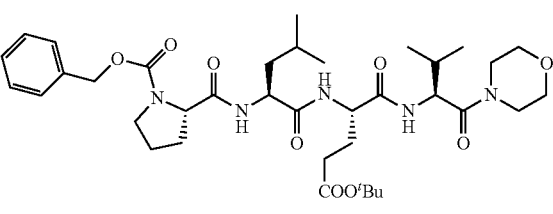
PW0540
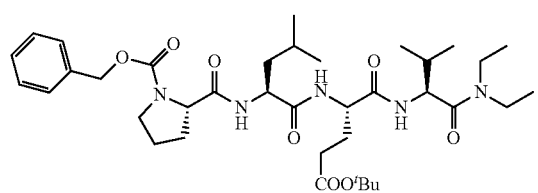
PW0541
PW0542
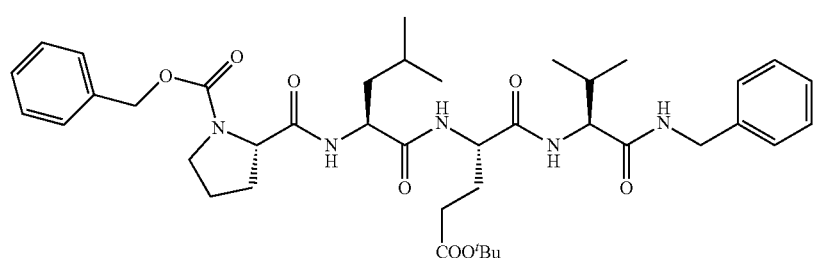
PW0543
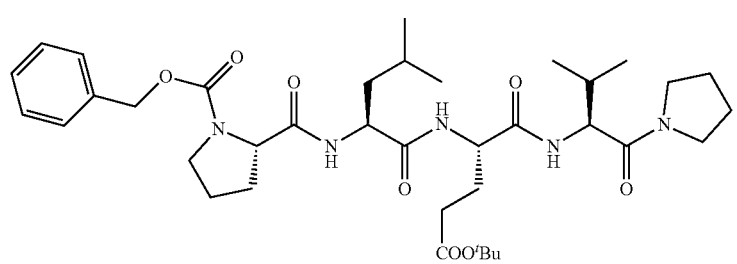

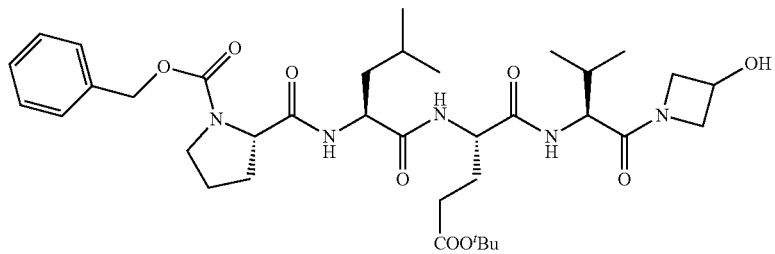
PW0544
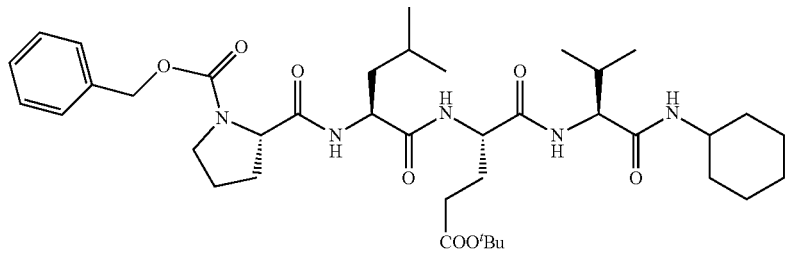
PW0545
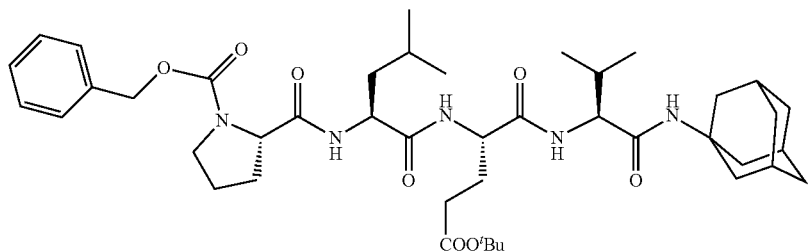
PW0547
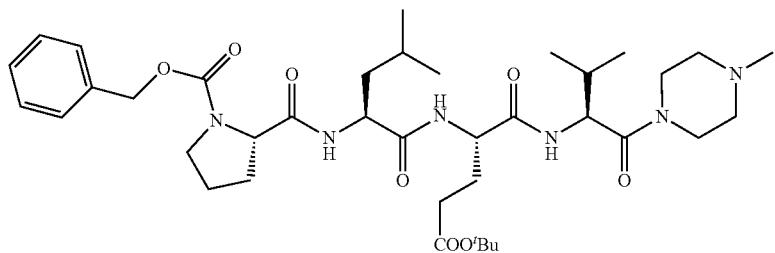
PW0559
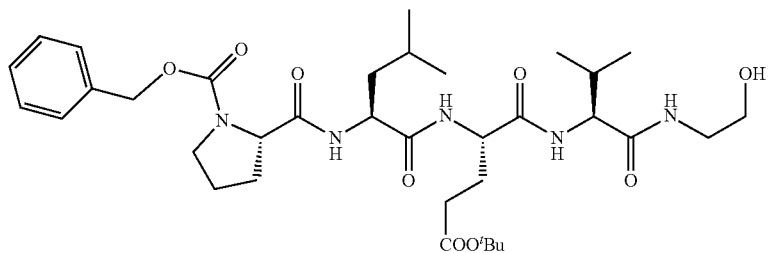
PW0561
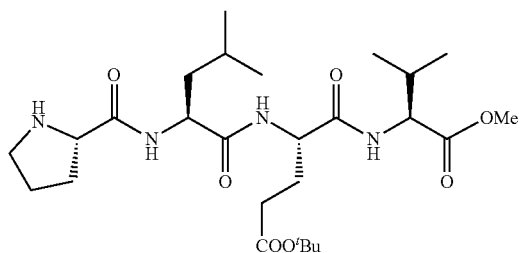
PW0539

In some embodiments of Formula I and pharmaceutically acceptable salts thereof:

$R^1$ is $R^6OCO—$;

$R^6$ is selected from the group consisting of alkyl, cycloalkyl, alkenyl, aryl, heteroaryl, and benzyl, wherein $R^6$ is optionally substituted with one or more chosen substituents chosen from —OH, —CN, —NH$_2$, and halogen;

$R^2$ is alkyl; and $R^3$ is OH, —OMe, allyloxy, or —NR$^8$R$^9$ and $R^8$ and $R^9$ is chosen from H or any of the following substituents:

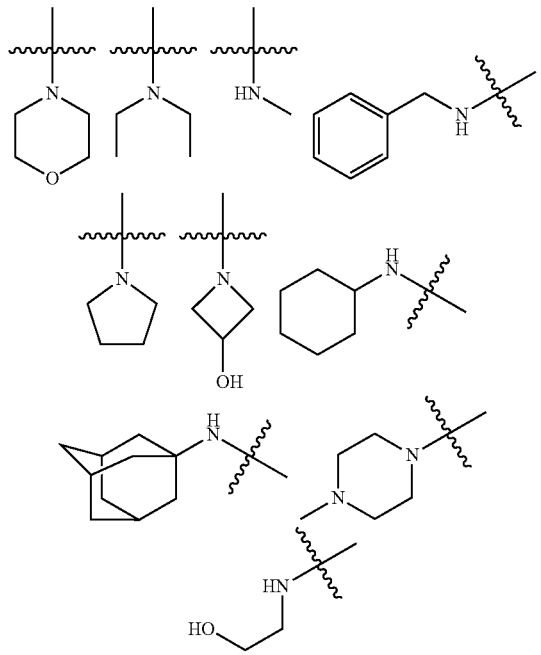

In some embodiments, $R^2$ is t-butyl.

In some embodiments, $R^1$ is $R^4CO$— wherein $R^4$ is 4-fluorophenyl.

In some embodiments, $R^4$, $R^5$, $R^6$ and $R^7$ is independently methyl or $nC_2$-$C_9$ alkyl.

In some embodiments, $R^4$, $R^5$, $R^6$ and $R^7$ is independently n-nonyl.

In some embodiments, $R^4$, $R^5$, $R^6$ and $R^7$ is independently 4-fluorophenyl.

2.1. Synthesis of Compounds of the Invention

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

Synthetic methods. The general methods used for the synthesis of various PW164 analogues (Series A-F) are depicted in Scheme 1 (below). Starting from commercially available Fmoc-Glu-OH 1, reaction with NH$_2$-Val-OMe 2 in the presence of the Hunig's base DIPEA and catalyzed by HBTU, followed by deprotection the Fmoc group in the presence of the base DEA will give intermediate 3. Coupling of 3 with Cbz-Pro-Leu-OH 4 by HBTU and DIPEA will provide intermediate 5. Deprotection of 5 by Pd/C and H$_2$ will lead to intermediate 6, which will react with various commercially available 7 to produce compounds of Series A. Series B and Series C will be generated in a similar fashion by reacting intermediate 6 with various commercially available 8 or 9. Intermediate 10 will be afforded by hydrolysis of the intermediate 5. 10 will react with various commercially available amines 11 to provide compounds of Series D. Hydrolyzing intermediate 5 using LiOH, followed by the treatment of 0.5% citric acid will afford intermediate 12 which will react with various commercially available alcohols 13 to provide compounds of Series E. Series F will be generated in a similar fashion by coupling of intermediate 12 with various commercially available amines 14.

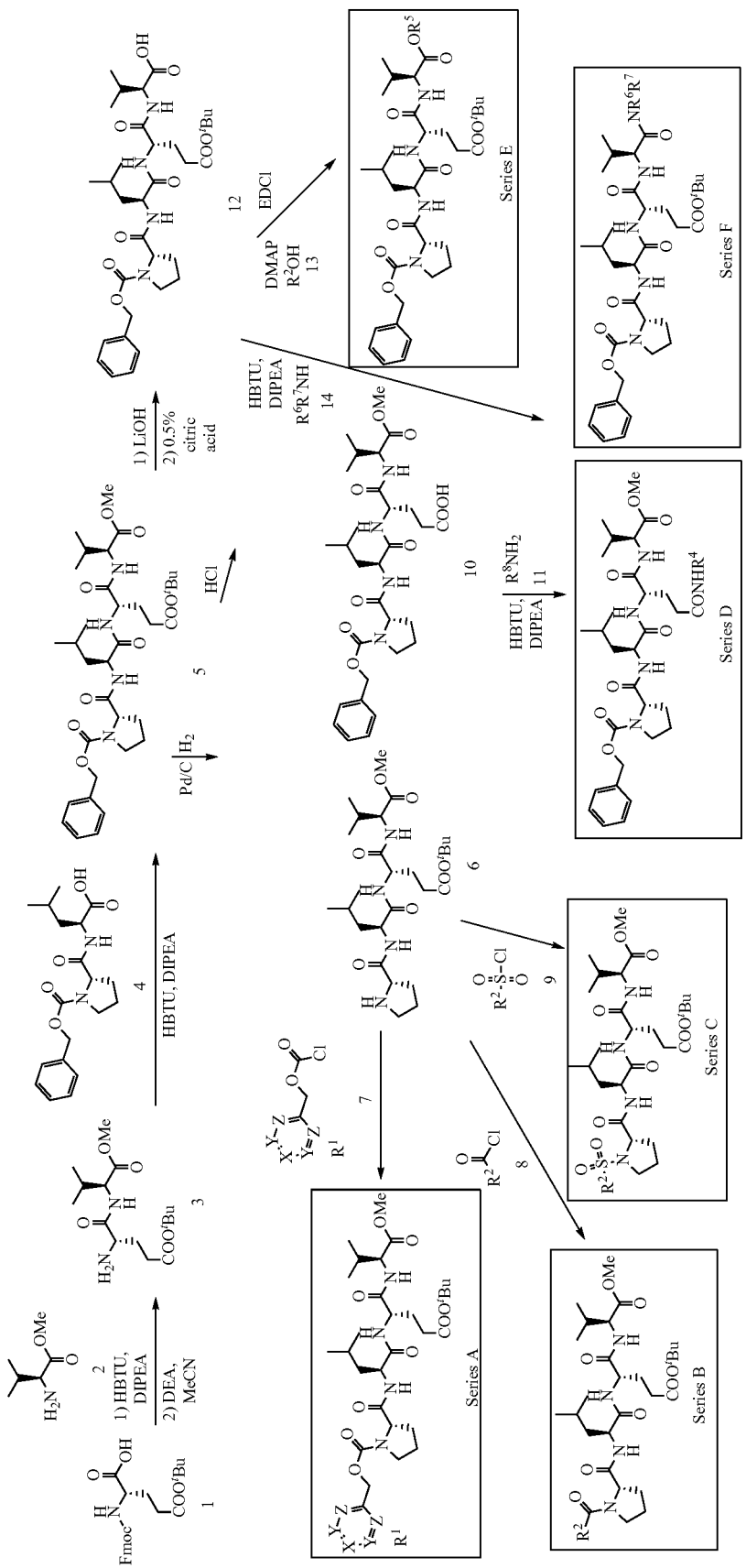

3.0. Method of Use

Nav1.6 channels amplify response to painful stimuli (hyperalgesia) through sustained firing of sensory neurons. Studies have shown that two splice isoforms of fibroblast growth factor 13 (FGF13), an accessory protein that binds to the Nav1.6 intracellular C-terminal tail4-7 differentially regulate channel function with FGF13-1a conferring protection against radicular pain and FGF13-1b exacerbating it. The inventors surprisingly discovered certain compounds, as exemplified by PW164, inhibits FGF13-1b and acts as a FGF13-1a mimetic.

In some embodiments, the invention encompasses a method of inhibiting FGF13-1b comprising contacting one or more cells with one or more compounds of Formula I or pharmaceutically acceptable salts thereof.

In some embodiments, the invention encompasses treating or alleviating pain by inhibiting FGF13-1b comprising administering one or more compounds of Formula I or pharmaceutically acceptable salts thereof to a subject.

4.0 Examples

4.1 Evidence for Functional Activity of PW164.

FGF13 stands out among iFGFs as a potent, specific, and diverse modulator of Nav channels, especially Nav1.6. When expressed in recombinant cells, FGF13 can suppress or augment Nav1.6-encoded currents and channel availability, depending on its N-terminal spliced isoform with phenotypes that are reminiscent of other iFGFs in these cell lines. In animal models of pain, the FGF13-1b isoform is up-regulated, while FGF13-1a exerts a protective effect. Models in DRG attribute the beneficial effect of the FGF13-1a isoform in pain to a specific effect on Nav1.6-mediated persistent and resurgent currents that are thought to take part in DRG firing associated with pain.

Figure 1:
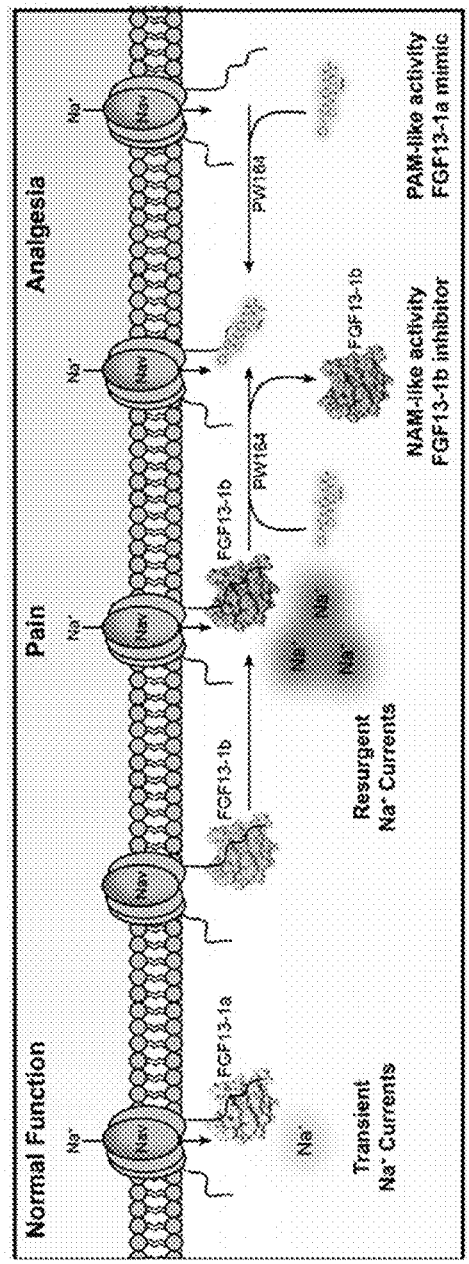
FIG. 1. Drug design strategy and mechanism of action of PW164. Under normal function, higher levels of FGF13-1a relative to FGF13-1b result in transient Na+ currents. Conversely, elevated levels of FGF13-1b lead to persistent Na+ currents that contribute to the sensation of pain by stimulating continuous firing in DRG neurons. PW164 might act as an analgesic by blocking FGF13-1b (NAM-like activity) and/or mimicking the effect of FGF13-1a (PAM-like activity).
Figure 2:
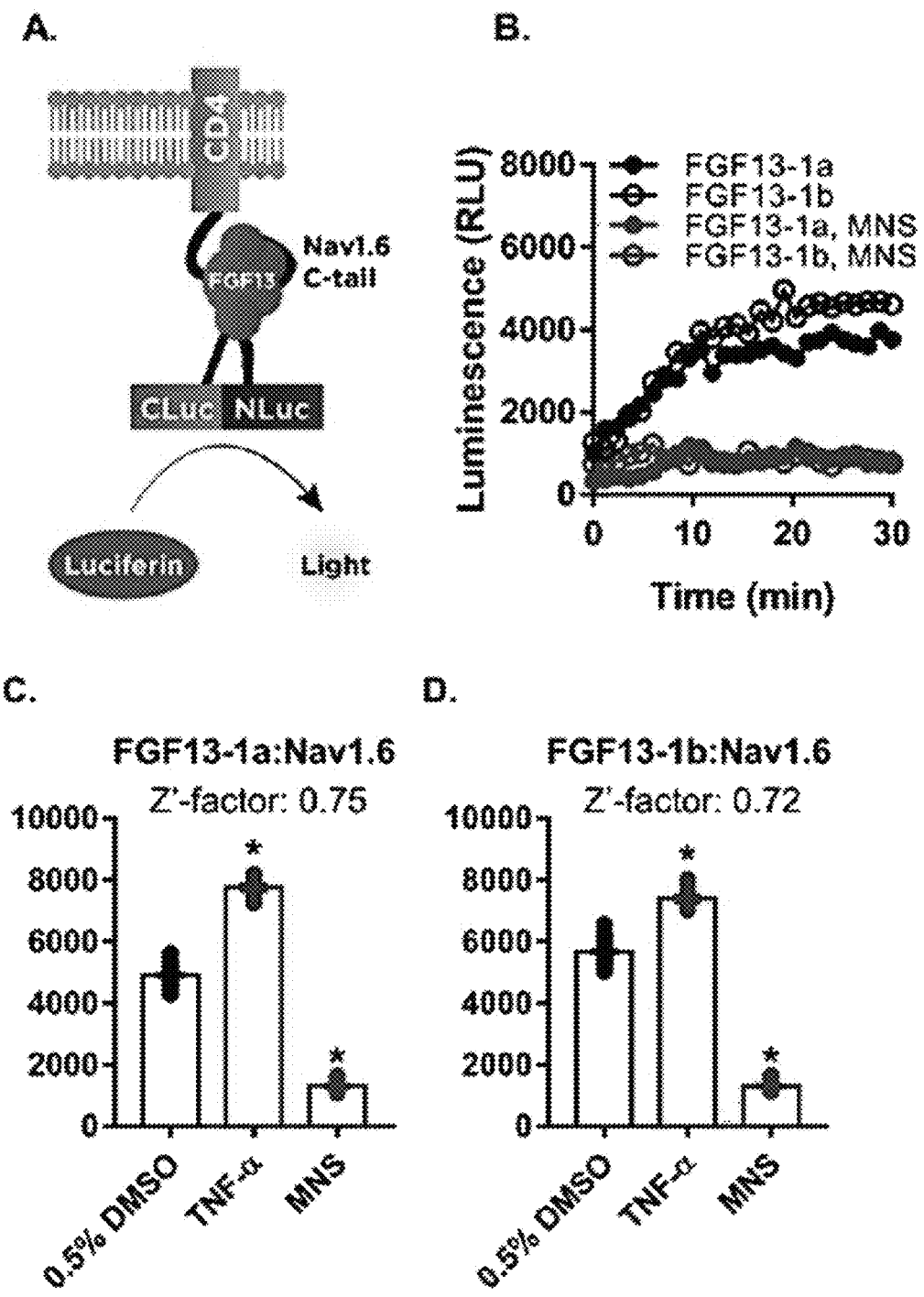
FIG. 2. In-cell reconstitution of FGF13: Nav1.6 complexes using the split-luciferase assay. A. Principle of split-luciferase assay. B. Luminescence-based complementation assay (LCA) of the FGF13-1a:Nav1.6 (solid dots) and FGF13-1b:Nav1.6 C-tail complex (open dots); control conditions are depicted in black; corresponding dark red dots refer to LCA complexes in the presence of the tyrosine kinase inhibitor MNS used as negative control. C,D. Summary bar graphs depicting assay robustness with respective Z' score calculations for each LCA complex. Green bars and dots refer to LCA conducted in the presence of tumor-necrosis factor-a, which increases assembly of FGF13:Nav1.6 complexes and was used as positive 20 control for assay optimization.
Figure 3:
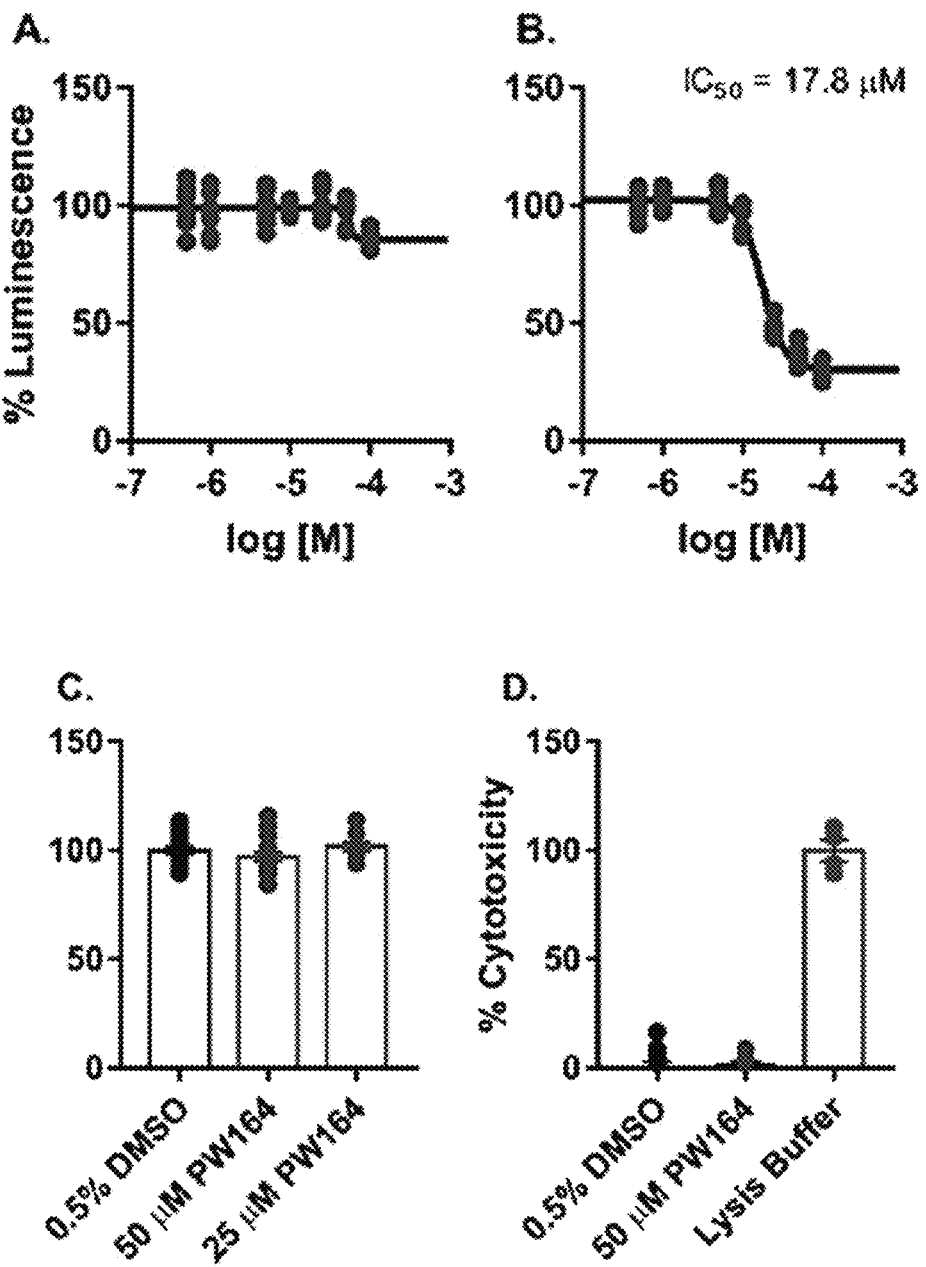
FIG. 3. PW164 inhibits FGF13-1b but not FGF13-1a binding to the Nav1.6 C-tail. Dose response of PW164 against the FGF13-1a:Nav1.6 (A) or FGF13-1b:Nav1.6 (B) complex by LCA reveals that PW164 prevents FGF13:Nav1.6 complex assembly (IC50=17.8 µM) but does not have a significant effect on FGF13-1A binding. Data are normalized with respect to 0.5% DMSO (vehicle). (C) PW164 has no effect on full length luciferase in transiently transfected HEK293 cells. (D) PW164 is not toxic toward HEK293 cells using the LDH cytotoxicity assay.
Figure 4:
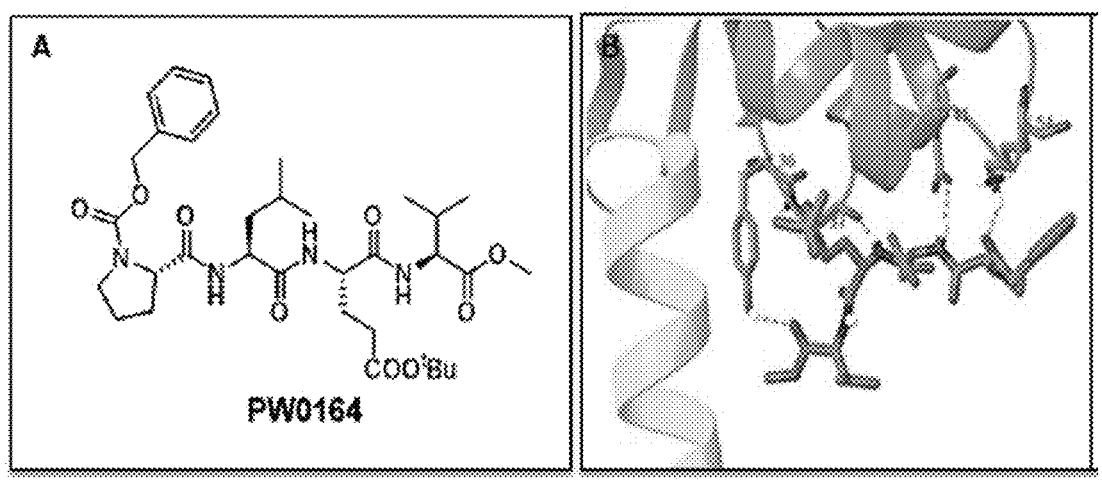
FIG. 4. The chemical structure of PW164 and predicted binding mode and molecular docking of PW164 and Nav1.6. A. The chemical structure of PW164. B. Predicted binding mode and molecular docking of PW164 and Nav1.6. Important residues are drawn in sticks. Hydrogen bonds are shown as dashed pink lines. C. Predicted binding mode of PW164 and Nav1.6 in 2D view.
Figure 4:
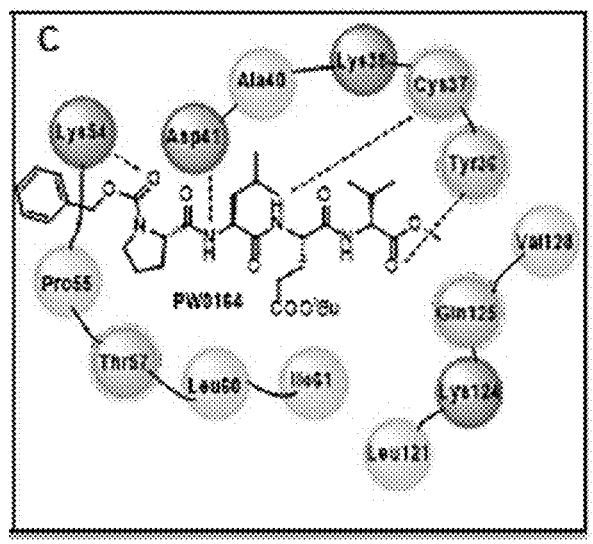
Figure 5:
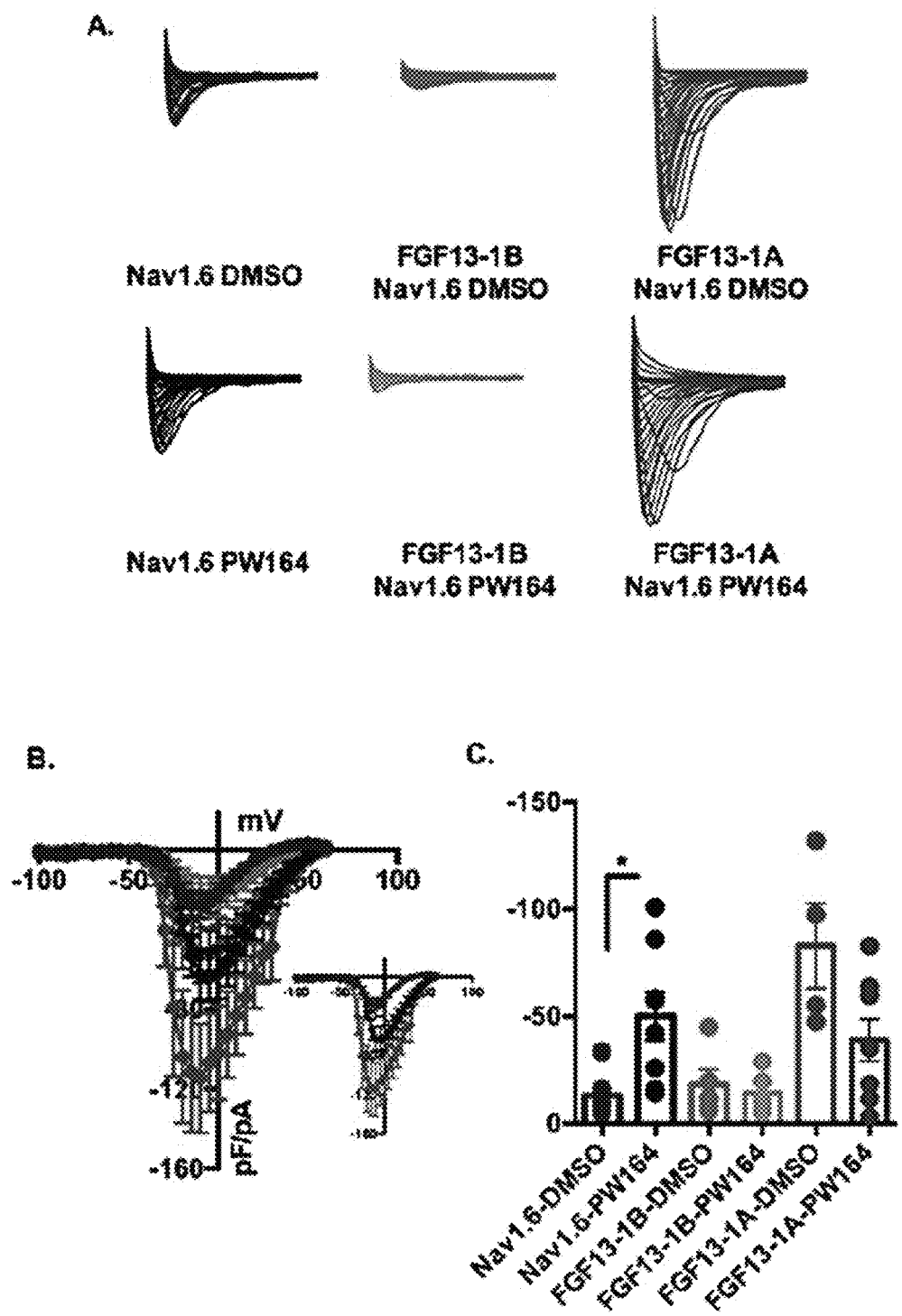
FIG. 5. PW164 acts as a FGF13-1a mimic on transient Na+ currents. A. Representative traces of Na+ transient currents (INa+) recorded from HEK-Nav1.6 cells transiently expressing the indicated constructs in response to depolarizing voltage steps in the presence of 50 µM PW164 or DMSO. B. Current-voltage relationship (I-V) derived from A. C. Summary bar graphs derived from A,B. Data are represented as mean±SEM; n=4-8 cells per group. *p<0.05; One-WAY ANOVA, post-hoc Bonferroni.
Figure 6:
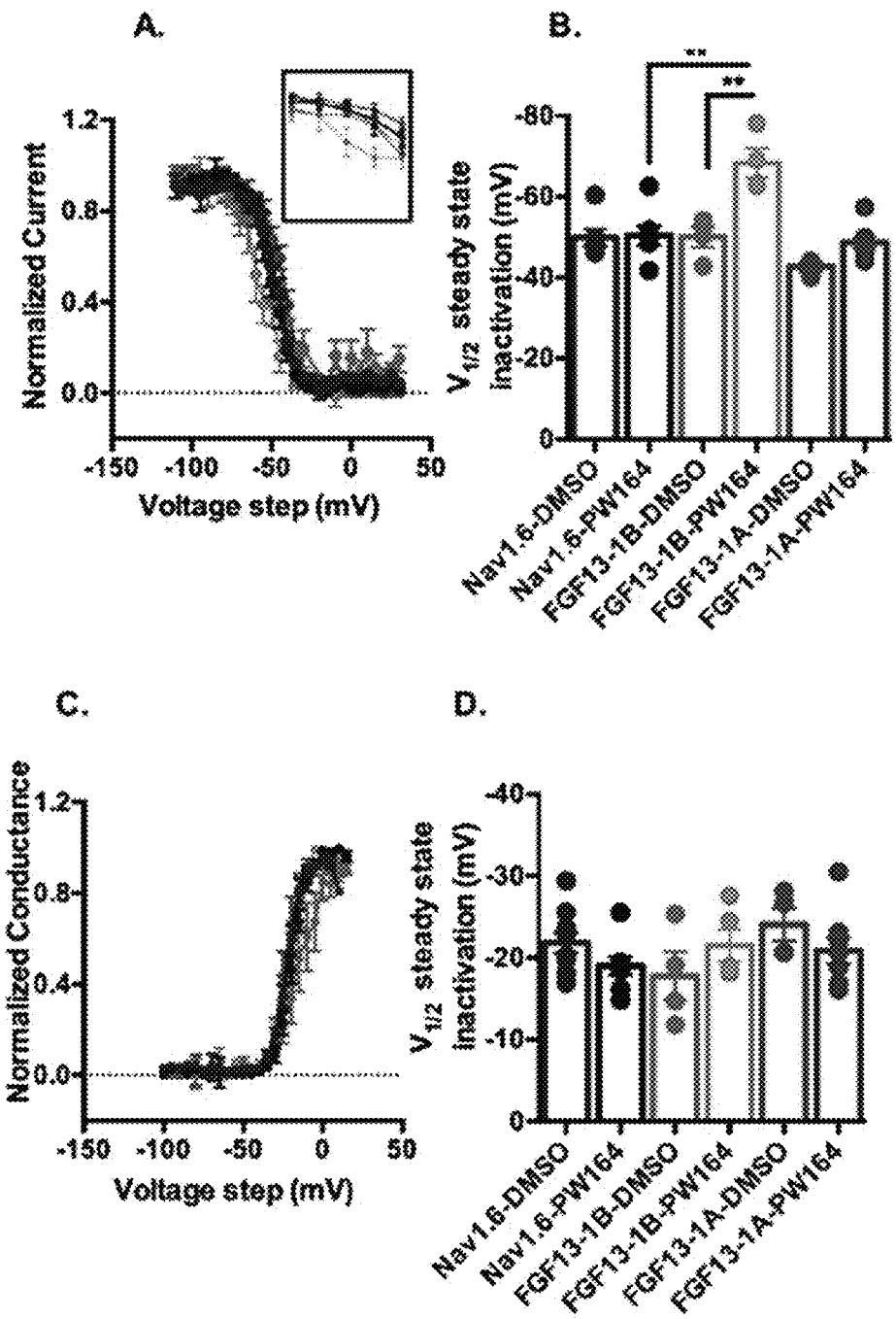
FIG. 6. PW164 decreases availability of FGF13-1b:Nav1.6 channel pool. HEK-Nav1.6 cells were transiently expressing GFP, FGF13-1b-GFP or FGF13-1a-GFP in the presence of DMSO (blue, red and dark red) 50 µM PW164 (black, green, dark green) A, Normalized current as a function of voltage (voltage dependence of steady-state inactivation) with Boltzmann fitting B Bar graph represents V1/2 of steady state inactivation. C. Normalized conductance (G/Gmax) as a function of voltage (voltage dependence of activation) with Boltzmann fitting. D. Bar graph represents V1/2 of activation. Data are represented as mean±SEM; n=4-8 cells per group. **p<0.01; One-WAY ANOVA, post-hoc Bonferroni.

Based on the success of other PPI regulators targeting ion channels we used the same rationale of selecting compounds that could act as a FGF13 isoform specific blocking FGF13-1b isoform effects mimicking FGF13-1a and select PW164 for functional assays. We used patch-clamp electrophysiology and begun functional validation of the lead compound using a panel of biophysical protocols targeting Nav channels (FIG. 5, 6). Strikingly, we found that PW164 not only reduces Nav1.6 channel availability in the presence of FGF13-1b (by causing a hyperpolarizing shift in the V1/2 of steady-state inactivation; FIG. 7B), but it retains an FGF13-1a mimic function on Na+ transient currents (FIG. 5C).

These studies provide a strong premise to further optimize PW164 improving its potency and refine even further isoform selectivity. In addition, the strength of interaction and phenotypic regulation of Na+ currents are strong for the FGF13: Nav1.6 pair, but FGF13 binds and regulates other neuronal (Nav1.1 and Nav1.2) and cardiac16,30 Nav channels and other iFGFs, such as cardiac FGF14, modulate Nav1.6 currents. Thus, cross reactivity of optimized leads against FGF13: Nav channel isoform complexes other than Nav1.6, (e.g, Nav1.1, Nav1.2, and the predominant cardiac iFGF: Nav pair) should be ruled out. Our structure-function studies provide a strong premise for divergence at the iFGFs: Nav channel interface, providing us with further confidence in developing selective compounds that lack undesired effects on other targets. Because our strategy has proven successful in targeting PPI within Nav channels, PW164-derived analogues are expected to rapidly translate into leads with limited side effects on other Nav channel isoforms.

4.2 Evidence of Efficacy in Behavioral Models of Clinical Pain

Nav1.6 has been shown to play a crucial role in nociceptor excitation eliciting pain. For example, peripherally-injected scorpion toxin Cn2, a potent and selective Nav1.6 activator, produces spontaneous pain and mechanical hypersensitivity (i.e., enhanced pain from mechanical stimulation) whereas knockdown of Nav1.6 expression in DRG strongly inhibits mechanical hypersensitivity and hyper-excitability of DRG neurons in animal models of neuropathic and inflammatory pain. These studies suggest that PW164 and its analogues, as regulators of Nav1.6 function, will affect nociceptor excitability and the intensity of pain. In a preliminary in vivo study, we tested effects of PW164 on nociceptive behavior in normal and capsaicin-injected mice. Intradermal capsaicin injection is known to strongly excite nociceptors at the injection site and sensitizes peripheral nociceptors and the spinal nociceptive neural circuit, resulting in mechanical hypersensitivity at the capsaicin injection site.

Figure 7:
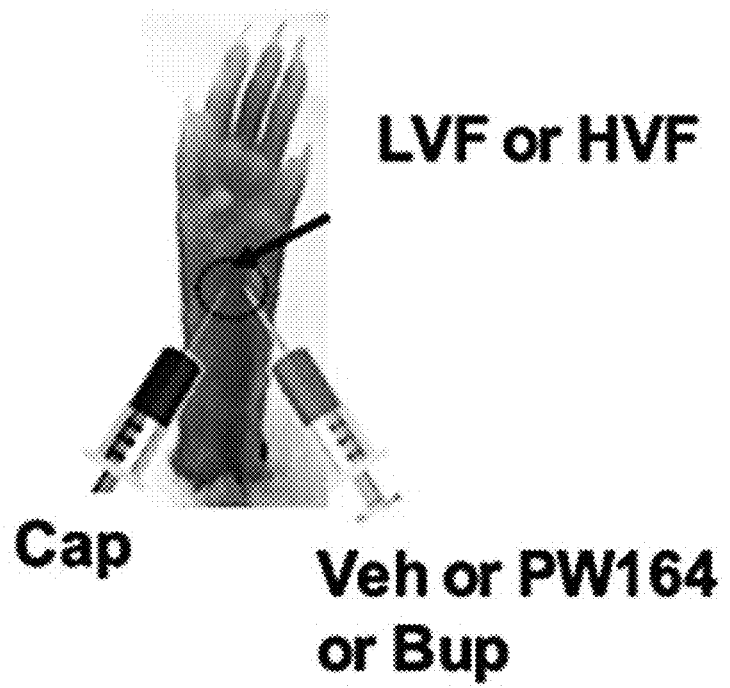
FIG. 7. Graphical representation of the capsaicin-induced pain model. After intraplantar capsaicin (Cap) injection, mice develop profound mechanical hypersensitivity to low- (LVF) and high-intensity von Frey filament (HVF) stimulations at the injection site, showing increased paw withdrawals from the stimulation (withdrawal response). Vehicle, PW164 or the local anesthetic bupivacaine (Bup) were injected later at the capsaicin injection site.
Figure 8:
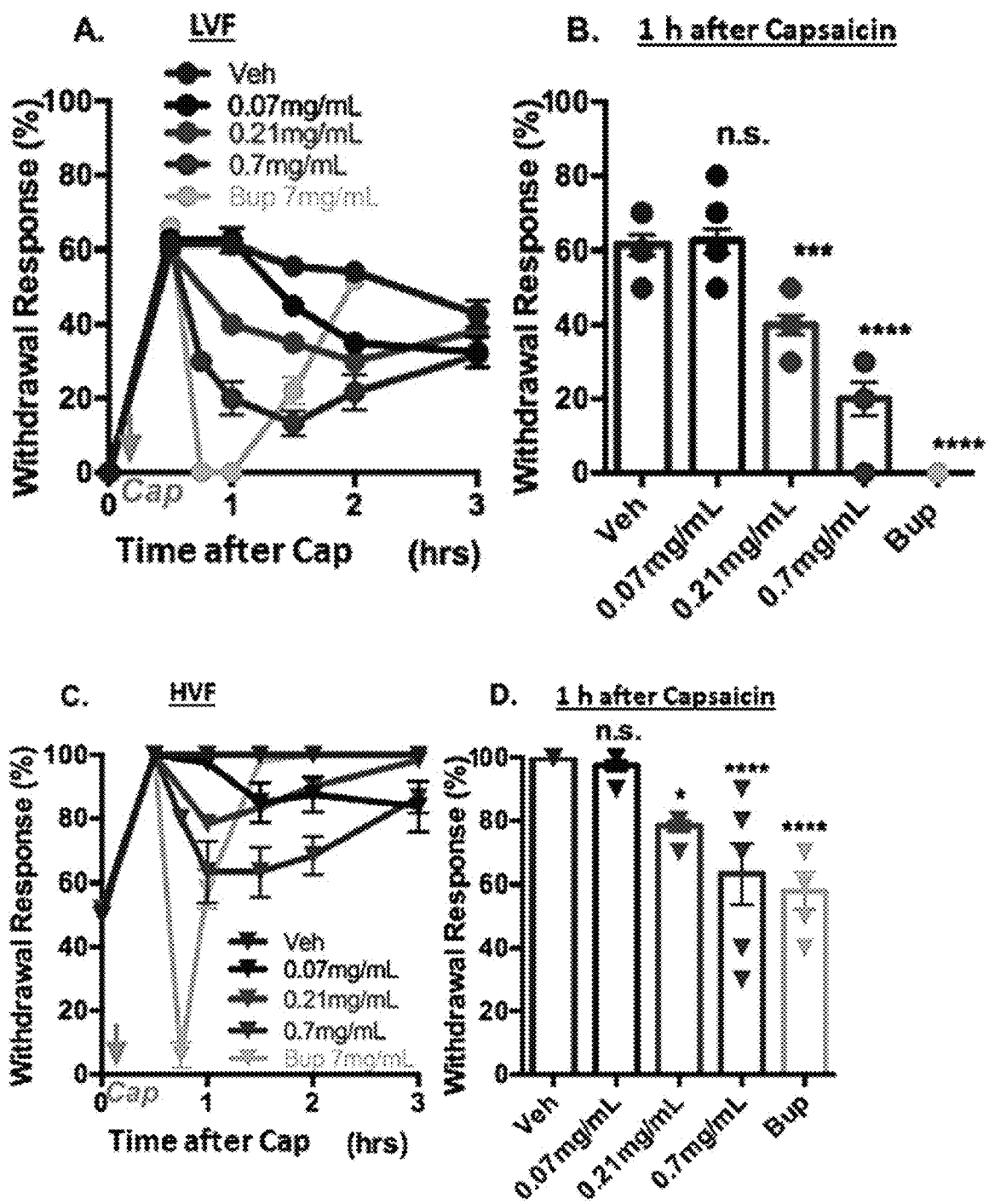
FIG. 8. Locally administered PW164 inhibits mechanical hypersensitivity in the capsaicin pain model. When administered to the capsaicin (Cap) injection site 30 min after the Cap injection, PW164 dose-dependently inhibits mechanical hypersensitivity to both low-intensity (LVF; A,B) and high-intensity (HVF; C,D) von Frey filament stimulations. Compared to the local anesthetic bupivacaine (Bup), PW164 shows longer-lasting effects without completely blocking mechanical sensation. PW164 and Bup were given at the indicated concentrations in a final injected volume of 3 ul. Bup 7 mg/ml corresponds to 0.7%; data are represented as mean #SEM; N=6-8 for each dose and time point. *p<0.05; *p<0.005;**p<0.001; One-way ANOVA, post-hoc Dunnett's.
Figure 9:
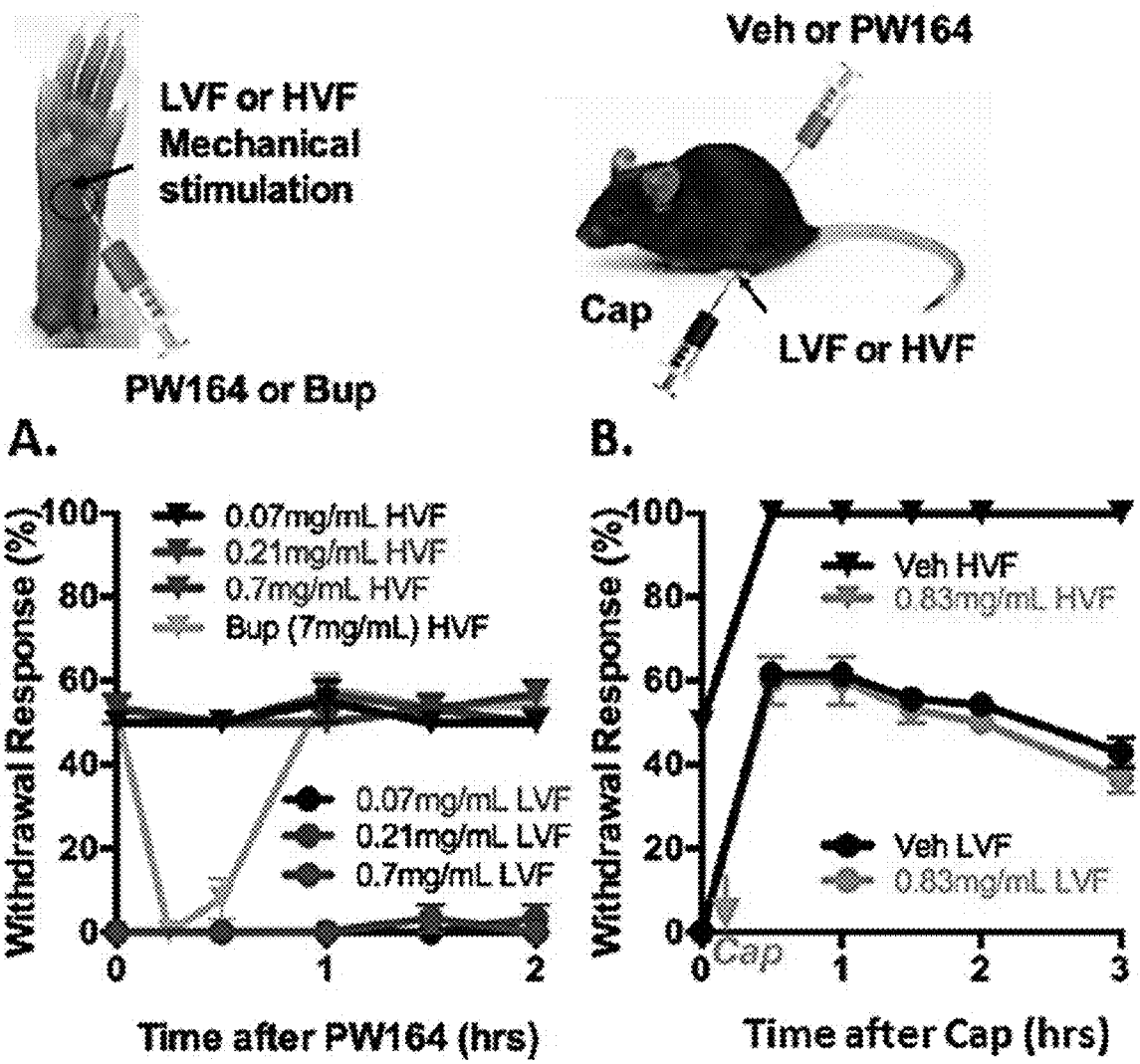
FIG. 9. PW164 suppresses pain without effects on normal mechanical sensitivity and spinal nociceptive function.

In animals, hypersensitivity is manifested as increased withdrawals from von Frey filament stimulations of the injection site (FIG. 7). In the preliminary study, we found that local administration of PW164 at the capsaicin injection site significantly alleviated the mechanical hypersensitivity (FIG. 8). By contrast, intrathecal administration of PW164 had no effect on the mechanical hypersensitivity (FIG. 9). In addition, when PW164 was locally administered at the normal skin, we did not observe any changes in normal mechanosensitivity (FIG. 9). These properties of PW164, namely its peripherally-limited action without an interference with normal sensory function, lead us to hypothesize that PW164 and its analogues will selectively inhibit "sensitized peripheral nociceptors" and thus be useful as non-opioid pain medications. We also found that PW164 administered at the surgical wound inhibits mechanical hypersensitivity in the plantar incision model (FIG. 10), a model of post-operative pain.

4.3 Synthetic Experimental Procedures of the Compounds:
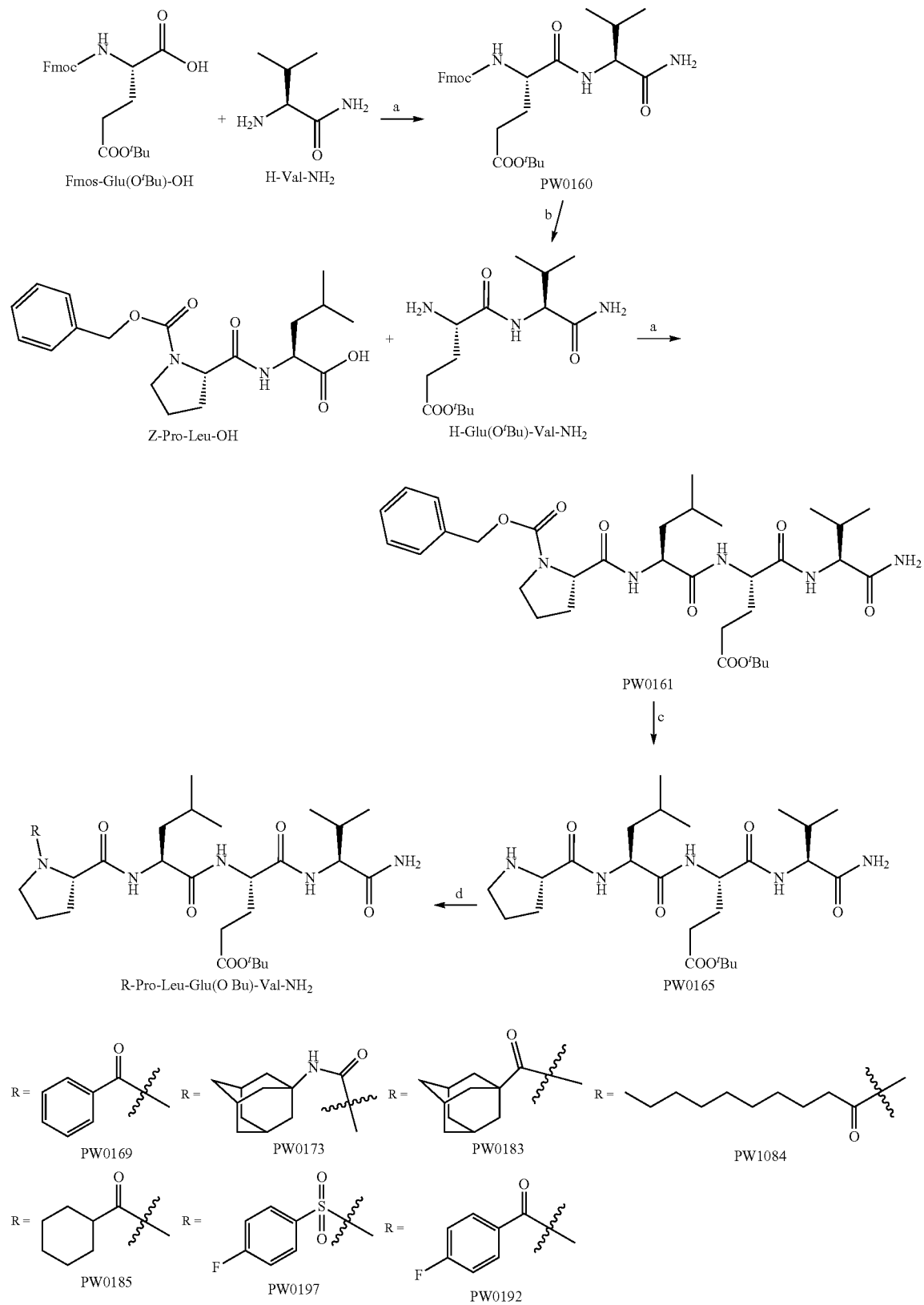
Reagents and conditions: (a) HBTU, HOBt, DIPEA, DCM; (b) DEA, MeCN, quant; (c) Pd/C, H₂; (d) HBTU, HOBt, DIPEA, DCM or TEA, DCM tert-Butyl (S)-4-(((((9H-fluoren-9-yl)methoxy)carbonyl)amino)-5-(((S)-1-amino-3-methyl-1-oxobutan-2-yl)amino)-5-oxopentanoate (PW0160)

Fmoc-Glu (O$^t$Bu)-OH (1.3 g, 3 mmol) and H-Val-NH$_2$·HCl (459 mg, 3 mmol) were dissolved in 20 mL DCM and the mixture solution was cooled to 0° C. with ice bath. HOBt (405 mg, 3 mmol), HBTU (2.3 g, 6 mmol) and DIPEA (2 mL, 12 mmol) were added to the solution at 0° C. Then removed the ice bath, and the mixture solution was stirred at room temperature overnight. After the reaction completed (detected by TLC), the mixture was washed with IN NaHSO$_4$, saturated NaHCO$_3$ and Brine. After drying over anhydrous Na$_2$SO$_4$, the solution was concentrated and purified with silica gel column (CH$_2$Cl$_2$/MeOH=50/1) to obtain PW0160 (1.3 g, 77%) as a white solid. $^1$H NMR (300 MHz, Methanol-d$_4$) δ 7.80 (d, J=7.5 Hz, 2H), 7.65 (d, J=6.1 Hz, 2H), 7.35 (dt, J=24.0, 7.7 Hz, 4H), 4.45-4.33 (m, 2H), 4.23 (dt, J=9.1, 4.5 Hz, 3H), 2.40-2.23 (m, 2H), 2.17-2.02 (m, 2H), 1.88 (s, 1H), 1.45 (d, J=2.3 Hz, 9H), 0.96 (td, J=7.0, 2.3 Hz, 6H). $^{13}$C NMR (75 MHz, Methanol-d$_4$) δ 172.74, 172.60, 157.05, 141.17, 127.37, 126.76, 124.78, 119.51, 80.44, 66.61, 58.15, 54.30, 47.52, 47.32, 47.03, 47.01, 46.75, 31.33, 30.63, 26.95, 18.34, 16.95.

Benzyl(S)-2-(((S)-1-(((S)-1-(((S)-1-amino-3-methyl-1-oxobutan-2-yl)amino)-5-(tert-butoxy)-1,5-dioxopentan-2-yl)amino)-4-methyl-1-oxopentan-2-yl)carbamoyl) pyrrolidine-1-carboxylate (PW0161)

To a solution of DEA (10 mL) and MeCN (10 mL) was added PW0160 (1.05 g, 2 mmol) and the solution was stirred at room temperature for 1 h. After the reaction completed, the solution was concentrated. The crude residue was dissolved in 20 mL dry DCM and added Z-Pro-Leu-OH (724, 2 mmol). The mixture solution was cooled to 0° C. with ice bath. HOBt (270 mg, 2 mmol), HBTU (1.5 g, 4 mmol) and DIPEA (1.3 mL, 8 mmol) were added to the solution at 0° C. Then removed the ice bath, and the mixture solution was stirred at room temperature overnight. After the reaction completed (detected by TLC), the mixture was washed with IN NaHSO$_4$, saturated NaHCO$_3$ and Brine. After drying over anhydrous Na$_2$SO$_4$, the solution was concentrated and purified with silica gel column (CH$_2$Cl$_2$/MeOH=50/1 to 20/1) to obtain PW0161 (0.96 g, 74%) as a white solid. $^1$H NMR (300 MHz, DMSO-d$_6$) δ 8.16-7.83 (m, 2H), 7.53 (dd, J=22.4, 8.9 Hz, 1H), 7.43-7.21 (m, 6H), 7.05 (s, 1H), 5.19-4.87 (m, 2H), 4.43-4.06 (m, 4H), 3.59-3.32 (m, 2H), 2.18 (ddd, J=17.3, 11.3, 7.1 Hz, 3H), 1.97-1.46 (m, 8H), 1.38 (d, J=3.0 Hz, 9H), 0.97-0.68 (m, 12H). $^{13}$C NMR (75 MHz, DMSO-d$_6$) δ 173.02, 172.54, 172.50, 172.40, 172.19, 171.11, 137.44, 128.82, 128.62, 128.22, 127.90, 127.28, 80.09, 66.37, 66.16, 60.29, 59.36, 57.68, 57.60, 52.20, 52.07, 51.65, 51.42, 47.57, 47.00, 41.05, 40.72, 31.62, 31.06, 30.99, 30.45, 28.20, 27.75, 27.60, 24.65, 24.57, 24.33, 23.39, 23.33, 22.02, 19.68, 18.11.

tert-Butyl(S)-5-(((S)-1-amino-3-methyl-1-oxobutan-2-yl)amino)-4-((S)-4-methyl-2-((S)-pyrrolidine-2-carboxamido) pentanamido)-5-oxopentanoate (PW0165)

To a solution of PW0161 (1.1 g) in 100 mL MeOH, 10% Pd/C (100 mg) was added. Under H$_2$, the mixture was allowed to stir at room temperature for 2 hrs. The solution was filtered, and the filtrate was concentrated to get the crude product. The residue was purified by silica gel column (CH$_2$Cl$_2$/EtOAc=50/1 to 25/1) to obtain PW0165 (793 mg, 91%) as a white solid. $^1$H NMR (300 MHz, Methanol-d$_4$) δ 4.54-4.39 (m, 2H), 4.23 (d, J=6.7 Hz, 1H), 3.69 (dd, J=8.7, 5.4 Hz, 1H), 3.33 (q, J=1.6 Hz, 1H), 2.96 (tdd, J=10.4, 6.3, 3.9 Hz, 2H), 2.34 (dt, J=8.6, 6.5 Hz, 2H), 2.21-2.01 (m, 3H), 1.98-1.59 (m, 7H), 1.46 (s, 9H), 1.06-0.88 (m, 12H). $^{13}$C NMR (75 MHz, Methanol-d$_4$) δ 175.81, 174.44, 173.34, 172.58, 171.94, 80.40, 60.11, 58.28, 52.46, 51.52, 47.33, 47.05, 46.76, 46.67, 40.82, 31.19, 30.70, 30.60, 26.98, 26.86, 25.67, 24.65, 22.01, 20.72, 18.38, 17.04.

tert-Butyl(S)-5-(((S)-1-amino-3-methyl-1-oxobutan-2-yl)amino)-4-((S)-2-((S)-1-benzoylpyrrolidine-2-carboxamido)-4-methylpentanamido)-5-oxopentanoate (PW0169)

PW0165 (102 mg, 0.2 mmol) was dissolved in 5 mL DCM and the solution was cooled to 0° C. with ice bath. Then Et$_3$N (65 mg, 0.5 mmol) and benzoyl chloride (42 mg, 0.3 mmol) were added. The mixture was stirred at room temperature for overnight. The solution was diluted with 20 mL of DCM and washed with IN NaHSO$_4$, saturated NaHCO$_3$ and Brine. After drying over anhydrous Na$_2$SO$_4$. the solution was concentrated and purified with silica gel column (CHCl$_3$/CH$_3$OH=50/1 to 20/1) to obtain PW0169 (104 mg, 85%) as a white solid. $^1$H NMR (300 MHz, Methanol-d$_4$) δ 7.62 (dd, J=7.6, 2.0 Hz, 2H), 7.56-7.38 (m, 5H), 4.60 (dd, J=8.1, 5.8 Hz, 1H), 4.44 (dt, J=9.8, 5.2 Hz, 3H), 4.22 (t, J=6.2 Hz, 2H), 3.79-3.65 (m, 2H), 3.58 (dd, J=6.8, 4.7 Hz, 1H), 2.44-2.27 (m, 4H), 2.15-1.80 (m, 9H), 1.67 (dt, J=8.5, 5.9 Hz, 2H), 1.45 (s, 9H), 1.42-1.37 (m, 4H), 1.01-0.95 (m, 12H), 0.85 (dd, J=12.7, 6.4 Hz, 2H). $^{13}$C NMR (75 MHz, Methanol-d$_4$) δ 173.53, 172.48, 172.07, 130.14, 128.05, 126.92, 126.40, 80.35, 60.72, 58.39, 52.66, 52.24, 50.31, 47.31, 47.03, 46.74, 40.18, 31.18, 30.53, 29.59, 26.96, 26.83, 25.01, 24.51, 22.05, 20.64, 18.37, 17.33, 17.02, 15.89.

tert-Butyl(S)-4-((S)-2-((S)-1-(((3R,5R,7R)-adamantan-1-yl)carbamoyl) pyrrolidine-2-carboxamido)-4-methylpentanamido)-5-(((S)-1-amino-3-methyl-1-oxobutan-2-yl)amino)-5-oxopentanoate (PW0173)

PW0165 (51 mg, 0.1 mmol) was dissolved in 5 mL DCM and the solution was cooled to 0° C. with ice bath. Then Et$_3$N (33 mg, 0.25 mmol) and 1-adamantyl isocyanate (18 mg, 0.1 mmol) were added. The mixture was stirred at room temperature overnight. The solution was diluted with 20 mL of DCM and washed with IN NaHSO$_4$, saturated NaHCO$_3$ and Brine. After drying over anhydrous Na$_2$SO$_4$. the solution was concentrated and purified with silica gel column (CHCl$_3$/CH$_3$OH=50/1 to 20/1) to obtain PW0173 (57 mg, 84%) as a white solid. $^1$H NMR (300 MHz, Methanol-d$_4$) δ 4.44 (dd, J=9.2, 5.4 Hz, 1H), 4.37-4.25 (m, 2H), 4.22 (d, J=6.6 Hz, 1H), 3.51 (d, J=7.1 Hz, 1H), 2.34 (td, J=7.6, 7.1, 2.5 Hz, 2H), 2.25-2.12 (m, 3H), 2.11-1.93 (m, 13H), 1.78-1.60 (m, 9H), 1.46 (s, 9H), 1.08-0.85 (m, 12H). $^{13}$C NMR (75 MHz, Methanol-d$_4$) δ 174.94, 173.76, 172.27, 80.38, 60.55, 58.63, 52.96, 52.56, 51.18, 46.29, 41.79, 40.07, 36.16, 31.26, 30.41, 29.66, 29.54, 26.95, 26.73, 24.60, 24.39, 22.01, 20.57, 18.34, 17.09.

tert-Butyl(S)-4-((S)-2-((S)-1-((3S,5S,7S)-adamantane-1-carbonyl) pyrrolidine-2-carboxamido)-4-methylpentanamido)-5-(((S)-1-amino-3-methyl-1-oxobutan-2-yl)amino)-5-oxopentanoate (PW0183)

PW0165 (51 mg, 0.1 mmol) and 1-adamantanecarboxylic acid (18 mg, 0.1 mmol) were dissolved in 5 mL DCM and the mixture solution was cooled to 0° C. with ice bath. HOBt (14 mg, 0.1 mmol), HBTU (76 mg, 0.2 mmol) and DIPEA (32 µL, 0.2 mmol) were added to the solution at 0° C. Then removed the ice bath, and the mixture solution was stirred at room temperature overnight. After the reaction completed (detected by TLC), the mixture was washed with 1N NaHSO$_4$, saturated NaHCO$_3$ and Brine. After drying over anhydrous Na$_2$SO$_4$, the solution was concentrated and purified with silica gel column (CH$_2$Cl$_2$/MeOH=50/1) to obtain PW0183 (49 mg, 73%) as a white solid. $^1$H NMR (300 MHz, Chloroform-d) δ 7.84 (d, J=6.2 Hz, 1H), 7.10 (d, J=9.0 Hz, 1H), 6.93-6.74 (m, 2H), 5.33 (s, 1H), 4.62 (s, 1H), 4.43 (dd, J=9.0, 5.3 Hz, 1H), 4.28 (q, J=6.3, 5.7 Hz, 1H), 4.16-4.04 (m, 1H), 3.97-3.65 (m, 3H), 3.18 (dd, J=7.5, 4.4 Hz, 1H), 2.45 (d, J=3.6 Hz, 3H), 2.24-2.00 (m, 11H), 1.83-1.66 (m, 7H), 1.52-1.37 (m, 15H), 1.11-0.80 (m, 12H). $^{13}$C NMR (75 MHz, Chloroform-d) δ 173.95, 171.68, 77.19, 62.79, 58.59, 55.18, 55.02, 54.04, 48.78, 42.18, 40.21, 38.18, 36.41, 32.34, 29.08, 28.13, 28.09, 26.56, 26.31, 26.19, 25.19, 23.19, 21.42, 19.47, 18.65, 17.48, 17.30.

tert-Butyl(S)-5-(((S)-1-amino-3-methyl-1-oxobutan-2-yl)amino)-4-((S)-2-((S)-1-decanoylpyrrolidine-2-carboxamido)-4-methylpentanamido)-5-oxopentanoate (PW0184)

PW0165 (51 mg, 0.1 mmol) and capric acid (17 mg, 0.1 mmol) were dissolved in 5 mL of DCM and the mixture solution was cooled to 0° C. with ice bath. HOBt (14 mg, 0.1 mmol), HBTU (76 mg, 0.2 mmol) and DIPEA (32 µL, 0.2 mmol) were added to the solution at 0° C. Then removed the ice bath, and the mixture solution was stirred at room temperature overnight. After the reaction completed (detected by TLC), the mixture was washed with 1N NaHSO$_4$, saturated NaHCO$_3$ and Brine. After drying over anhydrous Na$_2$SO$_4$, the solution was concentrated and purified with silica gel column (CH$_2$Cl$_2$/MeOH=50/1) to obtain PW0184 (48 mg, 72%) as a white solid. $^1$H NMR (300 MHz, DMSO-d$_6$) δ 8.33-7.77 (m, 2H), 7.65-7.24 (m, 2H), 7.06 (s, 1H), 4.44-4.04 (m, 4H), 3.69-3.40 (m, 3H), 2.32-1.60 (m, 12H), 1.39 (s, 12H), 1.26 (dd, J=11.1, 4.5 Hz, 14H), 0.84 (m, 14H). $^{13}$C NMR (75 MHz, DMSO-d$_6$) δ 173.06, 172.57, 172.40, 172.14, 171.21, 80.07, 60.13, 59.70, 57.82, 53.94, 52.36, 51.80, 42.19, 40.71, 40.40, 39.57, 34.25, 33.88, 32.15, 31.74, 31.67, 30.87, 29.66, 29.46, 29.39, 29.28, 29.20, 29.12, 28.20, 27.67, 27.38, 24.84, 24.78, 24.71, 24.63, 23.50, 23.44, 22.75, 22.54, 21.89, 19.68, 18.51, 18.11, 17.19, 14.39, 12.81.

tert-Butyl(S)-5-(((S)-1-amino-3-methyl-1-oxobutan-2-yl)amino)-4-((S)-2-((S)-1-(cyclohexanecarbonyl)pyrrolidine-2-carboxamido)-4-methylpentanamido)-5-oxopentanoate (PW0185)

PW0165 (51 mg, 0.1 mmol) and cyclohexanecarboxylic acid (13 mg, 0.1 mmol) were dissolved in 5 mL of DCM and the mixture solution was cooled to 0° C. with ice bath. HOBt (14 mg, 0.1 mmol), HBTU (76 mg, 0.2 mmol) and DIPEA (32 µL, 0.2 mmol) were added to the solution at 0° C. Then removed the ice bath, and the mixture solution was stirred at room temperature overnight. After the reaction completed (detected by TLC), the mixture was washed with 1N NaHSO$_4$, saturated NaHCO$_3$ and Brine. After drying over anhydrous Na$_2$SO$_4$, the solution was concentrated and purified with silica gel column (CH$_2$Cl$_2$/MeOH=50/1) to obtain PW0185 (51 mg, 82%) as a white solid. $^1$H NMR (300 MHz, Chloroform-d) δ 8.00 (s, 1H), 7.39 (s, 1H), 7.18 (s, 1H), 6.89 (s, 1H), 5.36 (s, 1H), 4.59 (s, 1H), 4.40 (s, 1H), 4.26 (d, J=8.6 Hz, 1H), 4.07 (s, 1H), 3.64 (d, J=33.5 Hz, 4H), 3.14 (d, J=7.9 Hz, 2H), 2.58-2.36 (m, 4H), 2.15 (t, J=31.3 Hz, 8H), 1.74 (s, 7H), 1.50 (d, J=8.4 Hz, 14H), 1.06-0.87 (m, 12H). $^{13}$C NMR (75 MHz, Chloroform-d) δ 174.08, 173.65, 173.09, 77.19, 60.34, 58.72, 55.10, 54.36, 54.17, 47.41, 42.78, 42.50, 40.04, 32.26, 29.27, 29.09, 28.43, 28.07, 27.53, 25.97, 25.67, 25.60, 25.49, 25.14, 24.95, 23.13, 21.17, 19.43, 18.62, 17.47, 17.33, 12.18.

tert-Butyl(S)-5-(((S)-1-amino-3-methyl-1-oxobutan-2-yl)amino)-4-((S)-2-((S)-1-(4-fluorobenzoyl) pyrrolidine-2-carboxamido)-4-methylpentanamido)-5-oxopentanoate (PW0192)

PW0192 (52 mg, 83%) was synthesized in a similar fashion as a white solid. $^1$H NMR (300 MHz, DMSO-d$_6$) δ 8.20-7.81 (m, 2H), 7.69-7.47 (m, 2H), 7.45-7.22 (m, 3H), 7.20-6.90 (m, 2H), 4.52-3.99 (m, 4H), 3.69-3.46 (m, 2H), 2.32-2.07 (m, 3H), 2.00-1.65 (m, 6H), 1.56-1.21 (m, 11H), 1.04-0.51 (m, 12H). $^{13}$C NMR (75 MHz, DMSO-d$_6$) δ 173.04, 172.17, 171.97, 171.13, 130.36, 130.24, 129.70, 115.69, 115.42, 80.09, 61.68, 60.59, 57.71, 51.68, 50.36, 40.69, 40.40, 39.84, 39.28, 31.61, 31.06, 30.97, 29.89, 28.19, 27.59, 25.34, 24.66, 24.30, 23.46, 22.74, 22.09, 21.68, 19.68, 18.12.

tert-Butyl(S)-5-(((S)-1-amino-3-methyl-1-oxobutan-2-yl)amino)-4-((S)-2-((S)-1-((4-fluorophenyl) sulfonyl) pyrrolidine-2-carboxamido)-4-methylpentanamido)-5-oxopentanoate (PW0197)

PW0197 (47 mg, 70%) was synthesized in a similar fashion as a white solid. $^1$H NMR (300 MHz, DMSO-d$_6$) δ 8.17 (d, J=8.2 Hz, 1H), 8.01 (d, J=7.9 Hz, 1H), 7.93 (dd, J=8.7, 5.2 Hz, 2H), 7.49 (dt, J=17.1, 8.7 Hz, 3H), 7.38 (s, 1H), 7.05 (s, 1H), 4.30 (t, J=8.4 Hz, 2H), 4.12 (q, J=7.6 Hz, 2H), 3.49-3.36 (m, 3H), 3.17 (d, J=9.0 Hz, 2H), 2.21 (q, J=8.4, 7.7 Hz, 2H), 1.92 (td, J=13.6, 6.5 Hz, 4H), 1.79-1.68 (m, 4H), 1.58-1.45 (m, 4H), 1.37 (s, 9H), 0.85 (dt, J=18.9, 7.0 Hz, 12H). $^{13}$C NMR (75 MHz, DMSO-d$_6$) δ 173.04, 172.34, 172.16, 171.36, 171.09, 130.92, 130.80, 117.06, 116.76, 80.08, 61.35, 57.61, 52.23, 51.32, 49.49, 41.14, 31.68, 31.22, 31.05, 28.19, 27.54, 24.62, 24.55, 23.53, 22.08, 19.68, 18.12.

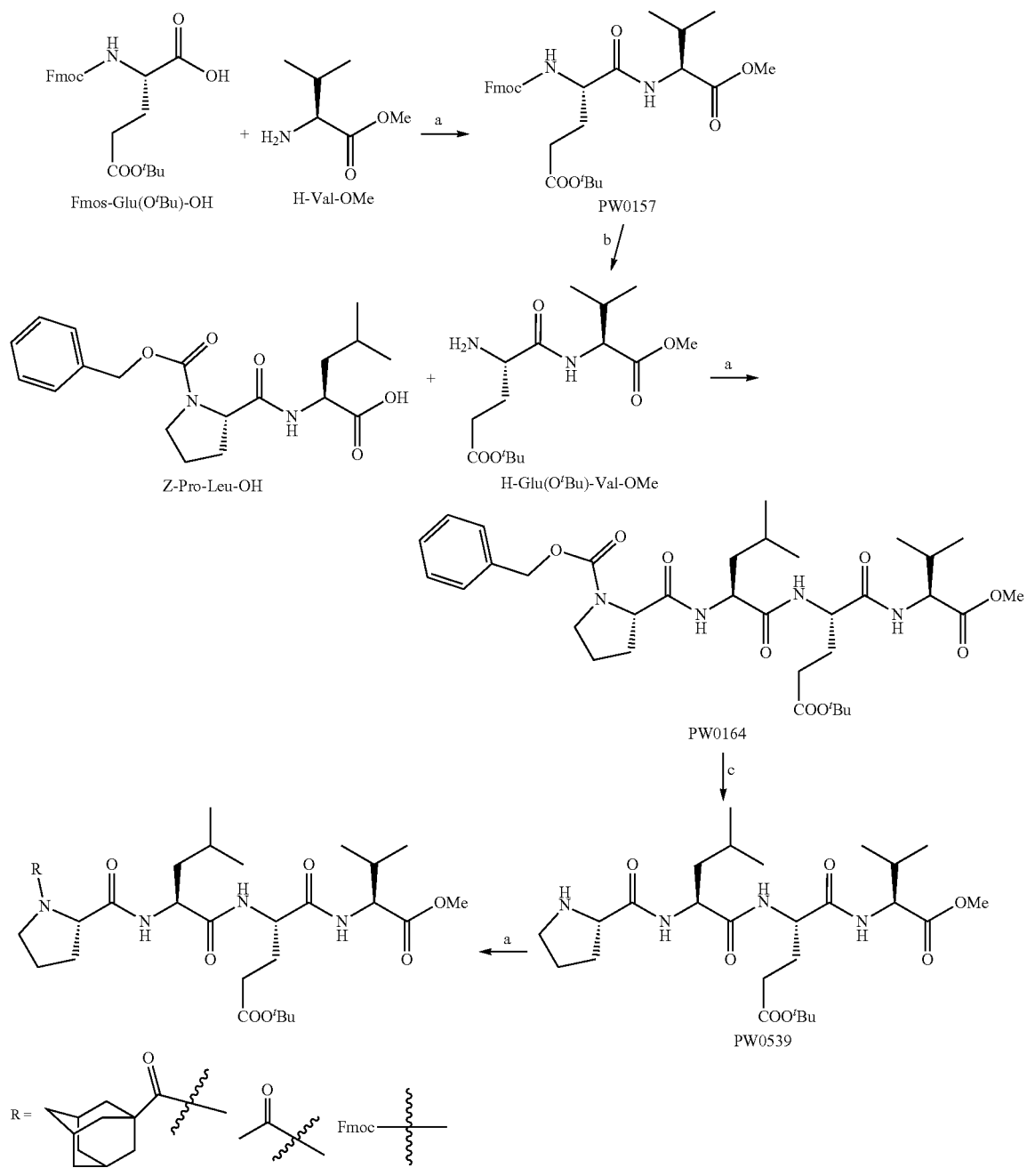

Reagents and conditions: (a) HBTU, HOBt, DIPEA, DCM; (b) DEA, MeCN, quant; (c) Pd/C, H₂.

tert-Butyl (S)-4-(((((9H-fluoren-9-yl)methoxy)carbonyl)amino-5-(((S)-1-methoxy-3-methyl-1-oxobutan-2-yl)amino)-5-oxopentanoate (PW0157)

Fmoc-Glu (O'Bu)-OH (1.3 g, 3 mmol) and H-Val-OMe·HCl (504 mg, 3 mmol) were dissolved in 20 mL of DCM and the mixture solution was cooled to 0° C. with ice bath. HOBt (405 mg, 3 mmol), HBTU (2.3 g, 6 mmol) and DIPEA (2 mL, 12 mmol) were added to the solution at 0° C. Then removed the ice bath, and the mixture solution was stirred at room temperature overnight. After the reaction completed (detected by TLC), the mixture was washed with 1N NaHSO₄, saturated NaHCO₃ and Brine. After drying over anhydrous Na₂SO₄, the solution was concentrated and purified with silica gel column (CH₂Cl₂/MeOH=50/1) to obtain PW0157 (1.53 g, 89%) as a white solid. ¹H NMR (300 MHz, Chloroform-d) δ 7.78 (d, J=7.4 Hz, 2H), 7.61 (d, J=7.4 Hz, 2H), 7.46-7.38 (m, 2H), 7.33 (td, J=7.4, 1.2 Hz, 2H), 6.98 (d, J=8.5 Hz, 1H), 5.77 (d, J=7.7 Hz, 1H), 4.53 (dd, J=8.6, 4.8 Hz, 1H), 4.45-4.37 (m, 2H), 4.25 (d, J=7.1 Hz, 2H), 3.75 (s, 3H), 2.46 (t, J=6.6 Hz, 2H), 2.29-1.94 (m, 3H), 1.49 (s, 9H), 0.96 (dd, J=8.9, 6.9 Hz, 6H).

Benzyl(S)-2-(((S)-1-(((S)-5-(tert-butoxy)-1-(((S)-1-methoxy-3-methyl-1-oxobutan-2-yl)amino)-1,5-dioxopentan-2-yl)amino)-4-methyl-1-oxopentan-2-yl)carbamoyl) pyrrolidine-1-carboxylate (PW0164)

To a solution of DEA (10 mL) and MeCN (10 mL) was added PW0157 (1.08 g, 2 mmol) and the solution was stirred at room temperature for 1 h. After the reaction completed, the solution was concentrated. The crude residue was dissolved in 20 mL of dry DCM and added Z-Pro-Leu-OH (724, 2 mmol). The mixture solution was cooled to 0° C. with ice bath. HOBt (270 mg, 2 mmol), HBTU (1.5 g, 4 mmol) and DIPEA (1.3 mL, 8 mmol) were added to the solution at 0° C. Then removed the ice bath, and the mixture solution was stirred at room temperature overnight. After the reaction completed (detected by TLC), the mixture was washed with 1N $NaHSO_4$, saturated $NaHCO_3$ and Brine. After drying over anhydrous $Na_2SO_4$, the solution was concentrated and purified with silica gel column ($CH_2Cl_2$/MeOH=50/1 to 20/1) to obtain PW0164 (1.24 g, 94%) as a light yellow solid. $^1$H NMR (300 MHz, Chloroform-d) δ 7.36 (s, 6H), 7.10 (d, J=8.6 Hz, 1H), 6.90-6.78 (m, 1H), 5.17 (s, 2H), 4.54-4.31 (m, 4H), 3.73 (s, 3H), 3.54 (d, J=8.3 Hz, 2H), 2.39 (dt, J=11.0, 7.3 Hz, 2H), 2.20 (pd, J=6.9, 5.3 Hz, 3H), 2.04-1.89 (m, 3H), 1.44 (s, 9H), 0.92 (ddd, J=13.8, 8.3, 5.4 Hz, 12H). $^{13}$C NMR (75 MHz, Chloroform-d) δ 173.07, 171.94, 171.02, 136.23, 128.53, 128.17, 127.86, 80.86, 67.54, 60.93, 57.51, 52.38, 52.03, 47.15, 40.45, 31.97, 30.79, 28.86, 28.07, 27.26, 25.02, 24.69, 22.94, 21.58, 18.99, 17.81. HRMS (ESI) calcd for C34H52N4O9 661.3813 (M+H)$^+$, found 661.3804.

tert-Butyl(S)-5-(((S)-1-methoxy-3-methyl-1-oxobutan-2-yl)amino)-4-((S)-4-methyl-2-((S)-pyrrolidine-2-carboxamido) pentanamido)-5-oxopentanoate (PW0539)

To a solution of PW0164 (1.0 g) in 100 mL MeOH, 10% Pd/C (100 mg) was added. Under $H_2$, the mixture was allowed to stir at room temperature for 12 hrs. The solution was filtered, and the filtrate was concentrated to get the crude product. The residue was purified by silica gel column ($CH_2Cl_2$/MeOH=20/1 to 15/1) to obtain PW0539 (733 mg, 92%) as a white solid. $^1$H NMR (300 MHz, Chloroform-d) δ 8.00 (d, J=8.3 Hz, 1H), 7.32-7.24 (m, 1H), 7.19 (d, J=8.5 Hz, 1H), 4.55-4.36 (m, 3H), 3.82 (dd, J=9.1, 5.3 Hz, 1H), 3.72 (s, 3H), 3.55-3.27 (m, 1H), 3.06-2.91 (m, 2H), 2.82 (s, 2H), 2.39 (q, J=6.9 Hz, 2H), 2.21-2.03 (m, 3H), 1.90 (tt, J=12.7, 6.4 Hz, 2H), 1.77-1.54 (m, 6H), 1.44 (s, 9H), 1.25 (t, J=7.1 Hz, 1H), 1.10 (t, J=7.2 Hz, 1H), 0.95-0.88 (m, 12H). $^{13}$C NMR (75 MHz, CDCl$_3$) δ 175.26, 173.22, 172.33, 171.98, 171.12, 80.98, 60.38, 57.53, 52.48, 52.04, 51.47, 47.22, 40.84, 31.73, 30.73, 30.67, 28.05, 27.46, 26.05, 24.93, 22.95, 21.78, 18.97, 17.75.

tert-Butyl(S)-4-((S)-2-((S)-1-(((3S,5S,7S)-adamantane-1-carbonyl) pyrrolidine-2-carboxamido)-4-methylpentanamido)-5-(((S)-1-methoxy-3-methyl-1-oxobutan-2-yl)amino)-5-oxopentanoate (PW0564)

PW0564 (46 mg, 67%) as a white solid. $^1$H NMR (300 MHz, Chloroform-d) δ 7.28-7.22 (m, 1H), 7.13 (d, J=8.6 Hz, 1H), 6.74 (d, J=7.0 Hz, 1H), 4.59 (q, J=3.8 Hz, 1H), 4.43 (td, J=8.3, 4.1 Hz, 2H), 4.29 (td, J=6.8, 3.7 Hz, 1H), 3.79 (ddd, J=18.8, 8.1, 3.4 Hz, 2H), 3.69 (s, 3H), 3.44-3.20 (m, 1H), 2.45-2.31 (m, 2H), 2.15 (dt, J=13.2, 6.7 Hz, 3H), 2.03-1.91 (m, 15H), 1.74-1.64 (m, 9H), 1.41 (s, 9H), 1.23 (s, 1H), 1.07 (t, J=7.1 Hz, 1H), 0.88 (dd, J=14.8, 6.5 Hz, 14H). $^{13}$C NMR (75 MHz, CDCl$_3$) δ 177.64, 172.75, 172.30, 172.02, 171.86, 171.10, 80.64, 62.28, 57.56, 52.60, 52.41, 51.91, 48.55, 42.01, 40.46, 38.14, 38.12, 36.58, 36.46, 32.01, 30.70, 28.30, 28.18, 28.03, 27.32, 24.94, 23.15, 21.50, 18.99, 17.94.

tert-Butyl(S)-4-((S)-2-((S)-1-acetylpyrrolidine-2-carboxamido)-4-methylpentanamido)-5-(((S)-1-methoxy-3-methyl-1-oxobutan-2-yl)amino)-5-oxopentanoate (PW0565)

PW0565 (45 mg, 78%) was synthesized in a similar fashion as a white solid. $^1$H NMR (300 MHz, Chloroform-d) δ 7.31-7.23 (m, 2H), 7.17 (d, J=8.5 Hz, 1H), 4.59-4.41 (m, 3H), 4.32 (ddd, J=9.3, 7.0, 4.7 Hz, 1H), 3.71 (s, 3H), 3.57 (q, J=5.5, 3.5 Hz, 1H), 3.46 (q, J=9.4, 8.6 Hz, 1H), 2.47-2.16 (m, 6H), 2.10 (s, 3H), 2.05-1.92 (m, 4H), 1.71 (d, J=12.9 Hz, 1H), 1.59 (dt, J=14.4, 7.6 Hz, 2H), 1.44 (s, 9H), 0.95-0.85 (m, 12H). $^{13}$C NMR (75 MHz, CDCl$_3$) δ 173.18, 172.04, 171.92, 171.70, 171.10, 80.85, 59.86, 57.49, 52.60, 52.48, 51.99, 48.29, 40.42, 31.87, 30.76, 28.07, 27.83, 27.38, 25.07, 24.97, 22.94, 22.43, 21.60, 18.98, 17.79.

(9H-Fluoren-9-yl)methyl(S)-2-(((S)-1-(((S)-5-(tert-butoxy)-1-(((S)-1-methoxy-3-methyl-1-oxobutan-2-yl)amino)-1,5-dioxopentan-2-yl)amino)-4-methyl-1-oxopentan-2-yl)carbamoyl) pyrrolidine-1-carboxylate (PW0576)

PW0576 (55 mg, 73%) was synthesized in a similar fashion as a white solid. $^1$H NMR (300 MHz, Chloroform-d) δ 7.78 (d, J=7.6 Hz, 2H), 7.60 (d, J=7.4 Hz, 2H), 7.42 (t, J=7.3 Hz, 2H), 7.33 (t, J=7.4 Hz, 2H), 7.28 (s, 1H), 7.08 (d, J=8.6 Hz, 1H), 6.85 (d, J=7.4 Hz, 1H), 4.51-4.22 (m, 7H), 3.73 (s, 3H), 3.60-3.41 (m, 2H), 3.34-3.19 (m, 1H), 2.40 (dq, J=16.0, 7.0, 5.8 Hz, 1H), 2.27-2.14 (m, 3H), 1.96 (s, 3H), 1.78-1.57 (m, 2H), 1.43 (s, 9H), 0.91 (ddd, J=13.9, 6.5, 4.0 Hz, 13H). $^{13}$C NMR (75 MHz, CDCl$_3$) δ 173.15, 171.90, 170.98, 156.35, 143.73, 141.33, 141.26, 127.78, 127.63, 127.08, 125.17, 124.95, 120.00, 119.86, 80.88, 67.81, 60.82, 57.48, 52.62, 52.31, 52.02, 47.20, 47.05, 41.75, 41.28, 40.49, 31.96, 30.78, 28.05, 27.29, 25.02, 24.74, 23.45, 22.94, 21.55, 18.99, 17.78, 14.19, 13.81.

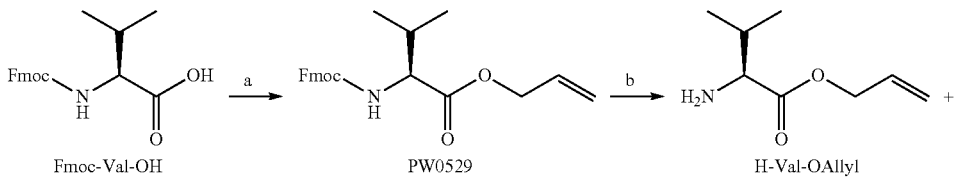

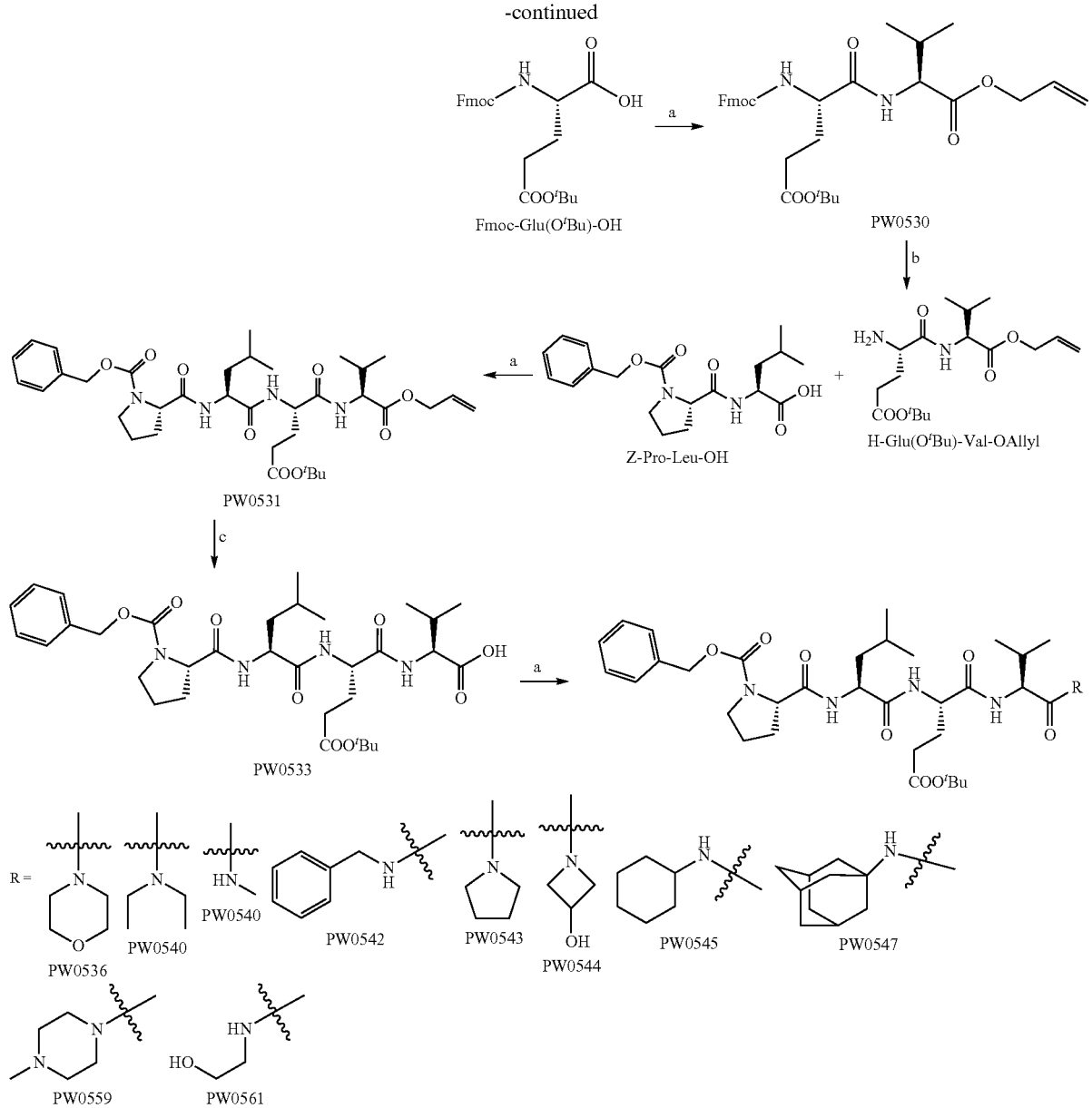

Reagents and conditions: (a) HBTU, HOBt, DIPEA, DCM; (b) DEA, MeCN, quant.

Allyl(((9H-fluoren-9-yl)methoxy)carbonyl)-L-valinate (PW0529)

To a solution of Fmoc-Val-OH (1.7 g, 5 mmol) in 5 mL dry DMF, $K_2CO_3$ (1.0 g, 7.5 mmol), allyl bromide (1.2 g, 10 mmol) and TBAB (161 mg, 0.5 mmol) were added. The mixture was stirred at room temperature for 16 h. After the reaction completed (detected by TLC), the mixture was diluted with 20 ml of water. Then the mixture was extracted with EtOAc (3×20 mL). The combined organic layer was washed with 1N $NaHSO_4$, saturated $NaHCO_3$ and Brine. After drying over anhydrous $Na_2SO_4$, the solution was concentrated and purified with silica gel column ($CH_2Cl_2$/MeOH=50/1 to 20/1) to obtain PW0529 (1.5 g, 76%) as a white solid. 1H NMR (300 MHz, Chloroform-d) δ 7.79 (dd, J=7.4, 1.1 Hz, 2H), 7.63 (d, J=7.5 Hz, 2H), 7.43 (tt, J=7.7, 1.4 Hz, 2H), 7.34 (tt, J=7.4, 1.1 Hz, 2H), 6.00-5.88 (m, 1H), 5.45-5.21 (m, 4H), 4.75-4.57 (m, 3H), 4.43 (d, J=7.1 Hz, 1H), 4.37 (dd, J=9.1, 4.8 Hz, 1H), 4.26 (t, J=7.0 Hz, 1H), 2.23 (td, J=6.9, 4.6 Hz, 1H), 1.03-0.93 (m, 6H). $^{13}C$ NMR (75 MHz, $CDCl_3$) δ 171.76, 156.21, 143.78, 141.31, 131.57, 127.69, 127.05, 125.08, 119.97, 119.02, 67.05, 65.86, 59.04, 47.23, 31.36, 18.99, 17.56.

tert-Butyl(S)-4-((((9H-fluoren-9-yl)methoxy)carbonyl)amino)-5-(((S)-1-(allyloxy)-3-methyl-1-oxobutan-2-yl)amino)-5-oxopentanoate (PW0530)

To a solution of DEA (10 mL) and MeCN (10 mL) was added PW0529 (1.5 g, 4 mmol) and the solution was stirred at room temperature for 1 h. After the reaction completed, the solution was concentrated. The crude residue was dissolved in 20 mL of dry DCM and added Fmoc-Glu (O'Bu)-OH (1.7, 4 mmol). The mixture solution was cooled to 0° C.

with ice bath. HOBt (540 mg, 4 mmol), HBTU (2.3 g, 6 mmol) and DIPEA (2.6 mL, 16 mmol) were added to the solution at 0° C. Then removed the ice bath, and the mixture solution was stirred at room temperature overnight. After the reaction completed (detected by TLC), the mixture was washed with 1N NaHSO$_4$, saturated NaHCO$_3$ and Brine. After drying over anhydrous Na$_2$SO$_4$, the solution was concentrated and purified with silica gel column (CH$_2$Cl$_2$/MeOH=50/1 to 20/1) to obtain PW0530 (1.5 g, 68%) as a white solid. $^1$H NMR (300 MHz, Chloroform-d) δ 7.78 (d, J=7.5 Hz, 2H), 7.61 (d, J=7.4 Hz, 2H), 7.42 (t, J=7.4 Hz, 2H), 7.33 (td, J=7.4, 1.2 Hz, 2H), 7.00 (d, J=8.6 Hz, 1H), 5.92 (tt, J=10.9, 5.4 Hz, 1H), 5.77 (d, J=7.7 Hz, 1H), 5.31 (dd, J=25.1, 13.9 Hz, 2H), 4.65 (s, 2H), 4.55 (dd, J=8.6, 4.7 Hz, 1H), 4.40 (dd, J=7.2, 2.1 Hz, 2H), 4.28 (dt, J=28.2, 6.7 Hz, 2H), 2.64-2.37 (m, 2H), 2.25 (dd, J=12.4, 6.4 Hz, 1H), 2.16-2.07 (m, 1H), 1.98 (dd, J=14.3, 7.2 Hz, 1H), 1.49 (s, 9H), 0.97 (dd, J=9.8, 6.9 Hz, 6H).

Benzyl(S)-2-(((S)-1-(((S)-1-(((S)-1-(allyloxy)-3-methyl-1-oxobutan-2-yl)amino)-5-(tert-butoxy)-1,5-dioxopentan-2-yl)amino)-4-methyl-1-oxopentan-2-yl)carbamoyl) pyrrolidine-1-carboxylate (PW0531)

PW0531 (1.46 g, 88%) was synthesized in a similar fashion as a white solid. $^1$H NMR (300 MHz, Chloroform-d) δ 7.36 (s, 5H), 7.12 (d, J=8.6 Hz, 1H), 6.83 (d, J=7.4 Hz, 1H), 5.92 (ddt, J=16.5, 11.0, 5.7 Hz, 1H), 5.34 (dq, J=17.2, 1.5 Hz, 1H), 5.28-5.21 (m, 1H), 5.17 (s, 2H), 4.63 (td, J=5.1, 4.4, 1.5 Hz, 2H), 4.53-4.31 (m, 4H), 3.53 (dd, J=12.6, 6.7 Hz, 2H), 2.50-2.34 (m, 2H), 2.30-2.12 (m, 3H), 2.05-1.83 (m, 4H), 1.44 (s, 10H), 0.98-0.82 (m, 12H). $^{13}$C NMR (75 MHz, CDCl$_3$) δ 173.09, 171.94, 171.11, 171.00, 166.59, 156.32, 136.25, 131.76, 128.53, 128.17, 127.86, 118.67, 80.84, 67.52, 65.66, 60.88, 57.49, 52.63, 52.32, 47.13, 40.50, 32.00, 30.82, 28.79, 28.07, 27.32, 25.00, 24.69, 22.95, 21.59, 19.03, 17.73.

Benzyl(S)-2-(((S)-1-(((S)-5-(tert-butoxy)-1-(((S)-3-methyl-1-morpholino-1-oxobutan-2-yl)amino)-1,5-dioxopentan-2-yl)amino)-4-methyl-1-oxopentan-2-yl)carbamoyl) pyrrolidine-1-carboxylate (PW0536)

To a solution of PW0531 (69 mg, 0.1 mmol) in CH$_2$Cl$_2$ (5 mL) at 0° C. was added Pd(PPh$_3$)$_4$ (12 mg, 0.01 mmol) and DEA (0.1 mL, 1 mmol). The reaction was stirred at room temperature for 10 h. After evaporation in vacuo, the residue was dissolved into CH$_2$Cl$_2$ (5 mL). The mixture solution was cooled to 0° C. with ice bath. Then morpholine (0.015 mL, 0.2 mmol) HOBt (14 mg, 40.1 mmol), HBTU (57 mg, 0.15 mmol) and DIPEA (0.07 mL, 0.4 mmol) were added to the solution at 0° C. After the removal of the ice bath, the mixture solution was stirred at room temperature overnight. The mixture was washed with 1N NaHSO$_4$, saturated NaHCO$_3$ and Brine. After drying over anhydrous Na$_2$SO$_4$, the solution was concentrated and purified with silica gel column (CH$_2$Cl$_2$/MeOH=50/1 to 20/1) to obtain PW0536 (57 g, 80%) as a white solid. $^1$H NMR (300 MHz, Chloroform-d) δ 7.34 (s, 5H), 7.27-7.17 (m, 1H), 7.12-6.64 (m, 1H), 5.16 (s, 2H), 4.67 (t, J=8.0 Hz, 1H), 4.49 (td, J=8.2, 5.0 Hz, 1H), 4.35 (q, J=7.6, 5.5 Hz, 2H), 3.87-3.48 (m, 10H), 3.35 (d, J=4.6 Hz, 2H), 2.98 (d, J=8.5 Hz, 2H), 2.49-1.82 (m, 10H), 1.77-1.49 (m, 3H), 1.42 (s, 10H), 1.01-0.77 (m, 12H). $^{13}$C NMR (75 MHz, CDCl$_3$) δ 172.61, 172.28, 172.01, 170.84, 169.76, 166.61, 156.14, 136.29, 128.50, 128.15, 127.81, 80.72, 67.48, 66.83, 66.72, 65.98, 60.90, 53.50, 52.76, 52.42, 50.61, 48.79, 47.12, 46.30, 42.42, 40.37, 38.57, 31.92, 31.00, 28.99, 28.06, 27.32, 24.98, 24.66, 22.90, 21.67, 19.64, 17.64.

Benzyl(S)-2-(((S)-1-(((S)-5-(tert-butoxy)-1-(((S)-1-(diethylamino)-3-methyl-1-oxobutan-2-yl)amino)-1,5-dioxopentan-2-yl)amino)-4-methyl-1-oxopentan-2-yl)carbamoyl) pyrrolidine-1-carboxylate (PW0540)

PW0540 (46 mg, 65%) was synthesized in a similar fashion as a white solid. $^1$H NMR (300 MHz, Chloroform-d) δ 7.31 (m, 5H), 7.05 (m, 2H), 5.16 (s, 2H), 4.81-4.19 (m, 4H), 3.48 (dq, J=32.6, 6.2, 5.5 Hz, 4H), 3.19 (dd, J=13.6, 7.0 Hz, 1H), 2.40-1.85 (m, 9H), 1.57 (d, J=31.5 Hz, 2H), 1.42 (d, J=2.0 Hz, 9H), 1.21 (t, J=7.1 Hz, 3H), 1.10 (t, J=7.0 Hz, 3H), 1.02-0.76 (m, 12H). $^{13}$C NMR (75 MHz, CDCl$_3$) δ 172.44, 171.90, 170.67, 170.51, 156.00, 136.42, 131.99, 128.54, 128.48, 128.45, 128.06, 127.80, 80.60, 67.36, 60.63, 53.87, 52.61, 47.08, 42.07, 40.68, 40.40, 31.71, 29.66, 28.92, 28.05, 24.88, 22.89, 21.80, 19.58, 19.49, 17.80, 14.62, 14.57, 12.87, 11.74.

Benzyl(S)-2-(((S)-1-(((S)-5-(tert-butoxy)-1-(((S)-3-methyl-1-(methylamino)-1-oxobutan-2-yl)amino)-1,5-dioxopentan-2-yl)amino)-4-methyl-1-oxopentan-2-yl)carbamoyl) pyrrolidine-1-carboxylate (PW0541)

PW0541 (56 mg, 86%) was synthesized in a similar fashion as a white solid. $^1$H NMR (300 MHz, Chloroform-d) δ 7.87 (d, J=6.2 Hz, 1H), 7.38 (s, 5H), 7.02 (d, J=5.2 Hz, 1H), 6.91 (d, J=9.3 Hz, 1H), 6.74 (s, 1H), 5.20 (s, 2H), 4.49-4.12 (m, 4H), 3.57 (d, J=7.2 Hz, 2H), 2.80 (d, J=4.7 Hz, 3H), 2.53-2.31 (m, 3H), 2.25-2.05 (m, 4H), 2.02-1.90 (m, 2H), 1.67 (d, J=10.8 Hz, 4H), 1.45 (s, 9H), 0.92 (dd, J=17.1, 6.0 Hz, 12H). $^{13}$C NMR (75 MHz, CDCl$_3$) δ 173.44, 173.18, 172.69, 171.55, 171.37, 156.59, 136.07, 128.61, 128.35, 127.82, 81.15, 67.73, 60.93, 58.68, 54.77, 53.71, 47.18, 40.22, 32.32, 29.15, 28.61, 28.08, 26.23, 25.10, 24.72, 22.96, 21.41, 19.44, 17.28.

Benzyl(S)-2-(((S)-1-(((S)-1-(((S)-1-(benzylamino)-3-methyl-1-oxobutan-2-yl)amino)-5-(tert-butoxy)-1,5-dioxopentan-2-yl)amino)-4-methyl-1-oxopentan-2-yl)carbamoyl) pyrrolidine-1-carboxylate (PW0542)

PW0542 (57 mg, 75%) was synthesized in a similar fashion as a white solid. $^1$H NMR (300 MHz, Chloroform-d) δ 7.87 (d, J=6.4 Hz, 1H), 7.37 (s, 5H), 7.28 (s, 5H), 7.22-7.16 (m, 2H), 7.09 (d, J=8.7 Hz, 1H), 6.99 (d, J=5.7 Hz, 1H), 5.18 (s, 2H), 4.59-4.27 (m, 6H), 3.52 (t, J=7.2 Hz, 2H), 2.40 (s, 4H), 2.20-1.93 (m, 6H), 1.60 (s, 2H), 1.44 (s, 9H), 0.92 (dd, J=17.3, 6.1 Hz, 12H). $^{13}$C NMR (75 MHz, CDCl$_3$) δ 173.21, 172.90, 172.53, 172.09, 171.49, 171.02, 156.41, 138.66, 136.14, 128.57, 128.26, 127.83, 127.64, 126.84, 81.01, 67.65, 60.92, 58.65, 54.48, 53.40, 47.12, 43.26, 40.35, 39.84, 32.24, 29.59, 28.75, 28.08, 26.56, 25.01, 24.69, 22.89, 21.56, 19.53, 19.46, 17.52.

Benzyl(S)-2-(((S)-1-(((S)-5-(tert-butoxy)-1-(((S)-3-methyl-1-oxo-1-(pyrrolidin-1-yl) butan-2-yl)amino)-1,5-dioxopentan-2-yl)amino)-4-methyl-1-oxopentan-2-yl)carbamoyl) pyrrolidine-1-carboxylate (PW0543)

PW0543 (53 mg, 76%) was synthesized in a similar fashion as a white solid. $^1$H NMR (300 MHz, Chloroform-d) δ 7.34 (s, 5H), 7.21 (d, J=8.6 Hz, 1H), 7.15 (t, J=4.3 Hz, 1H), 6.98 (s, 1H), 5.16 (s, 2H), 4.44 (dt, J=41.0, 6.4 Hz, 4H), 3.73-3.38 (m, 7H), 2.29 (d, J=7.9 Hz, 2H), 2.08-1.83 (m, 10H), 1.41 (s, 9H), 0.89 (dt, J=11.9, 5.0 Hz, 12H). $^{13}$C NMR (75 MHz, CDCl$_3$) δ 172.54, 172.28, 171.99, 170.83, 169.72, 156.04, 136.38, 128.46, 128.06, 127.80, 80.63, 67.37, 60.73, 56.03, 52.67, 49.44, 47.08, 46.72, 45.84, 40.12, 31.09, 29.65, 29.01, 28.05, 27.60, 26.01, 25.07, 24.91, 24.16, 22.89, 19.45, 17.87.

Benzyl(S)-2-(((S)-1-(((S)-5-(tert-butoxy)-1-(((S)-1-(3-hydroxyazetidin-1-yl)-3-methyl-1-oxobutan-2-yl)amino)-1,5-dioxopentan-2-yl)amino)-4-methyl-1-oxopentan-2-yl)carbamoyl) pyrrolidine-1-carboxylate (PW0544)

PW0544 (46 mg, 66%) was synthesized in a similar fashion as a white solid. $^1$H NMR (300 MHz, Chloroform-d) δ 7.51 (s, 1H), 7.35 (s, 5H), 7.15 (d, J=8.7 Hz, 1H), 6.87 (s, 1H), 5.17 (s, 2H), 4.64-3.99 (m, 9H), 3.55 (q, J=8.1, 6.8 Hz, 2H), 2.45-1.81 (m, 10H), 1.75-1.50 (m, 3H), 1.43 (s, 9H), 0.91 (d, J=6.5 Hz, 12H). $^{13}$C NMR (75 MHz, CDCl$_3$) δ 172.75, 172.46, 171.26, 170.74, 156.43, 136.44, 128.53, 128.19, 127.80, 80.92, 67.56, 61.25, 60.37, 58.26, 57.61, 54.34, 53.68, 52.92, 47.20, 40.29, 31.94, 28.07, 27.26, 25.04, 24.67, 22.91, 21.63, 19.19, 18.14.

Benzyl(S)-2-(((S)-1-(((S)-5-(tert-butoxy)-1-(((S)-1-(cyclohexylamino)-3-methyl-1-oxobutan-2-yl)amino)-1,5-dioxopentan-2-yl)amino)-4-methyl-1-oxopentan-2-yl)carbamoyl) pyrrolidine-1-carboxylate (PW0545)

PW0545 (54 mg, 74%) was synthesized in a similar fashion as a white solid. $^1$H NMR (300 MHz, Chloroform-d) δ 7.85 (d, J=6.4 Hz, 1H), 7.34 (d, J=14.5 Hz, 5H), 7.04 (d, J=5.4 Hz, 1H), 7.00 (s, 1H), 6.64 (s, 1H), 5.18 (s, 2H), 4.49-4.24 (m, 4H), 3.72 (s, 1H), 3.55 (q, J=7.4, 6.5 Hz, 2H), 2.38 (d, J=7.1 Hz, 2H), 2.13 (dq, J=16.0, 8.6, 7.1 Hz, 6H), 1.90 (dt, J=24.2, 9.1 Hz, 6H), 1.77-1.50 (m, 8H), 1.43 (s, 9H), 1.34 (d, J=3.0 Hz, 2H), 1.24-1.13 (m, 3H), 0.90 (dd, J=15.6, 7.7 Hz, 12H). $^{13}$C NMR (75 MHz, CDCl$_3$) δ 173.12, 172.54, 171.32, 169.82, 156.41, 136.16, 128.55, 128.28, 127.84, 80.93, 67.65, 61.01, 58.64, 54.85, 54.35, 53.38, 48.34, 47.16, 40.41, 39.93, 33.39, 32.90, 32.70, 32.25, 29.57, 28.88, 28.07, 26.64, 25.57, 25.04, 25.00, 24.72, 22.89, 21.58, 19.40, 17.45.

Benzyl(S)-2-(((S)-1-(((S)-1-(((S)-1-(((3R,5R,7R)-adamantan-1-yl)amino)-3-methyl-1-oxobutan-2-yl)amino)-5-(tert-butoxy)-1,5-dioxopentan-2-yl)amino)-4-methyl-1-oxopentan-2-yl)carbamoyl) pyrrolidine-1-carboxylate (PW0547)

PW0547 (55 mg, 71%) was synthesized in a similar fashion as a white solid. $^1$H NMR (300 MHz, Chloroform-d) δ 7.69 (d, J=5.3 Hz, 1H), 7.37 (s, 5H), 6.95 (d, J=13.6 Hz, 2H), 6.08 (s, 1H), 5.18 (s, 2H), 4.60-4.19 (m, 4H), 3.54 (s, 2H), 2.38 (s, 3H), 2.13 (d, J=7.6 Hz, 3H), 2.01 (d, J=13.1 Hz, 13H), 1.88 (s, 2H), 1.66 (s, 9H), 1.44 (s, 9H), 0.93 (d, J=6.6 Hz, 8H). $^{13}$C NMR (75 MHz, CDCl$_3$) δ 173.09, 172.35, 171.93, 171.14, 169.84, 169.78, 156.38, 136.19, 132.14, 132.01, 128.55, 128.51, 128.27, 127.84, 80.88, 80.67, 67.62, 60.93, 59.13, 53.97, 53.16, 51.99, 47.15, 41.47, 41.26, 40.51, 36.40, 32.22, 29.70, 29.47, 29.42, 28.08, 26.77, 25.03, 24.72, 23.09, 22.91, 21.59, 19.46, 19.37, 18.03, 17.58.

Benzyl(S)-2-(((S)-1-(((S)-5-(tert-butoxy)-1-(((S)-3-methyl-1-(4-methylpiperazin-1-yl)-1-oxobutan-2-yl)amino)-1,5-dioxopentan-2-yl)amino)-4-methyl-1-oxopentan-2-yl)carbamoyl) pyrrolidine-1-carboxylate (PW0559)

PW0559 (44 mg, 60%) was synthesized in a similar fashion as a white solid. $^1$H NMR (300 MHz, Chloroform-d) δ 7.34 (s, 5H), 7.18 (d, J=8.3 Hz, 1H), 6.91 (s, 1H), 5.16 (s, 2H), 4.74 (t, J=7.7 Hz, 1H), 4.50 (q, J=8.1, 5.5 Hz, 1H), 4.36 (q, J=8.2, 5.5 Hz, 2H), 3.74-3.45 (m, 6H), 2.39 (t, J=9.6 Hz, 5H), 2.30 (s, 4H), 2.18-1.87 (m, 6H), 1.57 (d, J=37.3 Hz, 3H), 1.42 (s, 9H), 1.06-0.81 (m, 12H). $^{13}$C NMR (75 MHz, CDCl$_3$) δ 172.57, 172.14, 171.91, 170.75, 169.51, 156.12, 136.34, 128.48, 128.10, 127.81, 80.68, 67.42, 60.78, 55.14, 54.68, 53.45, 52.71, 52.31, 47.09, 45.91, 45.68, 41.99, 40.56, 31.87, 31.22, 29.66, 28.91, 28.07, 27.49, 24.94, 24.66, 22.89, 21.75, 19.76, 19.69, 17.45.

Benzyl(S)-2-(((S)-1-(((S)-5-(tert-butoxy)-1-(((S)-1-((2-hydroxyethyl)amino)-3-methyl-1-oxobutan-2-yl)amino)-1,5-dioxopentan-2-yl)amino)-4-methyl-1-oxopentan-2-yl)carbamoyl) pyrrolidine-1-carboxylate (PW0561)

PW0561 (22 mg, 32%) was synthesized in a similar fashion as a white solid. $^1$H NMR (300 MHz, Chloroform-d) δ 8.07 (d, J=5.7 Hz, 1H), 7.38 (s, 5H), 7.17 (d, J=4.4 Hz, 1H), 7.02-6.88 (m, 2H), 5.20 (s, 2H), 4.44 (ddd, J=32.9, 8.5, 4.6 Hz, 2H), 4.17 (dd, J=35.1, 5.7 Hz, 2H), 3.68 (d, J=11.4 Hz, 2H), 3.56 (tt, J=7.2, 3.9 Hz, 2H), 3.35 (d, J=5.8 Hz, 1H), 2.50-2.34 (m, 2H), 2.14 (dq, J=8.0, 5.0 Hz, 3H), 2.05-1.87 (m, 3H), 1.65 (dd, J=9.4, 4.4 Hz, 2H), 1.45 (s, 9H), 0.97-0.81 (m, 12H). $^{13}$C NMR (75 MHz, CDCl$_3$) δ 174.04, 173.55, 173.47, 172.76, 171.43, 171.36, 156.71, 135.98, 128.63, 128.61, 128.41, 127.83, 81.32, 67.83, 61.73, 60.97, 58.40, 55.51, 54.31, 47.21, 42.84, 40.25, 32.42, 29.68, 28.94, 28.56, 28.09, 25.93, 25.07, 24.73, 22.82, 21.55, 19.54, 19.49, 17.34.

tert-Butyl (4S)-4-((2S)-2-((2S)-1-((1R,3R)-adamantane-1-carbonyl) pyrrolidine-2-carboxamido)-4-methylpentanamido)-5-(((S)-1-methoxy-3-methyl-1-oxobutan-2-yl)amino)-5-oxopentanoate (PW0564)

PW0564 (46 mg, 67%) was synthesized in a similar fashion as a white solid. $^1$H NMR (300 MHz, Chloroform-d) δ 7.28-7.22 (m, 1H), 7.13 (d, J=8.6 Hz, 1H), 6.74 (d, J=7.0 Hz, 1H), 4.59 (q, J=3.8 Hz, 1H), 4.43 (td, J=8.3, 4.1 Hz, 2H), 4.29 (td, J=6.8, 3.7 Hz, 1H), 3.79 (ddd, J=18.8, 8.1, 3.4 Hz, 2H), 3.69 (s, 3H), 3.44-3.20 (m, 1H), 2.45-2.31 (m, 2H), 2.15 (dt, J=13.2, 6.7 Hz, 3H), 2.03-1.91 (m, 15H), 1.74-1.64 (m, 9H), 1.41 (s, 9H), 1.23 (s, 1H), 1.07 (t, J=7.1 Hz, 1H), 0.88 (dd, J=14.8, 6.5 Hz, 14H).

tert-Butyl(S)-4-((S)-2-((S)-1-acetylpyrrolidine-2-carboxamido)-4-methylpentanamido)-5-(((S)-1-methoxy-3-methyl-1-oxobutan-2-yl)amino)-5-oxopentanoate (PW0565)

PW0565 (45 mg, 83%) was synthesized in a similar fashion as a white solid. $^1$H NMR (300 MHz, Chloroform-d) δ 7.31-7.23 (m, 2H), 7.17 (d, J=8.5 Hz, 1H), 4.59-4.41 (m, 3H), 4.32 (ddd, J=9.3, 7.0, 4.7 Hz, 1H), 3.71 (s, 3H), 3.57 (q, J=5.5, 3.5 Hz, 1H), 3.46 (q, J=9.4, 8.6 Hz, 1H), 2.47-2.16

(m, 6H), 2.10 (s, 3H), 2.05-1.92 (m, 4H), 1.71 (d, J=12.9 Hz, 1H), 1.59 (dt, J=14.4, 7.6 Hz, 2H), 1.44 (s, 9H), 0.95-0.85 (m, 12H).

tert-Butyl (4S)-4-((2S)-2-(1-(2-((9H-fluoren-9-yl) methoxy)-2-oxoacetyl) pyrrolidine-2-carboxamido)-4-methylpentanamido)-5-(((S)-1-methoxy-3-methyl-1-oxobutan-2-yl)amino)-5-oxopentanoate (PW0576)

PW0576 was synthesized in a similar fashion as a white solid. $^1$H NMR (300 MHz, Chloroform-d) δ 7.78 (d, J=7.6 Hz, 2H), 7.60 (d, J=7.4 Hz, 2H), 7.42 (t, J=7.3 Hz, 2H), 7.33 (t, J=7.4 Hz, 2H), 7.28 (s, 1H), 7.08 (d, J=8.6 Hz, 1H), 6.85 (d, J=7.4 Hz, 1H), 4.51-4.22 (m, 7H), 3.73 (s, 3H), 3.60-3.41 (m, 2H), 3.34-3.19 (m, 1H), 2.40 (dq, J=16.0, 7.0, 5.8 Hz, 1H), 2.27-2.14 (m, 3H), 1.96 (s, 3H), 1.78-1.57 (m, 2H), 1.43 (s, 9H), 0.91 (ddd, J=13.9, 6.5, 4.0 Hz, 13H).

It is to be understood that both the foregoing general description of the invention and the following detailed description are exemplary, and thus do not restrict the scope of the invention.

All publications mentioned herein are incorporated by reference to the extent they support the present invention.

We claim:

1. A compound of Formula I or a pharmaceutically acceptable salt thereof:

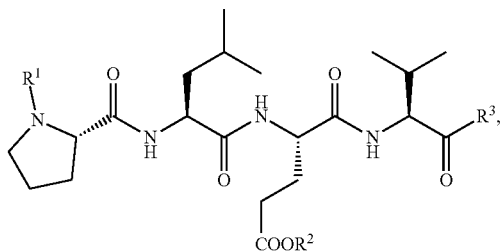

Formula I wherein: $R^1$ is H, alkyl, cycloalkyl, aryl, heteroaryl, $R^4CO—$, $R^5NHCO—$, $R^6OCO—$, $R^7SO_2—$, or fluorenylmethoxycarbonyl protecting group (Fmoc);
wherein $R^4$, $R^5$, $R^6$ and $R^7$ are independently selected from the group consisting of alkyl, cycloalkyl, alkenyl, aryl, heteroaryl, adamantyl, and benzyl, and each of $R^4$, $R^5$, $R^6$ and $R^7$ is optionally substituted with one or more substituents selected from the group consisting of —OH, —CN, —NH$_2$, and halogen;
$R^2$ is alkyl, aryl, heteroaryl, or cycloalkyl; and
$R^3$ is OH, alkoxy, allyloxy,

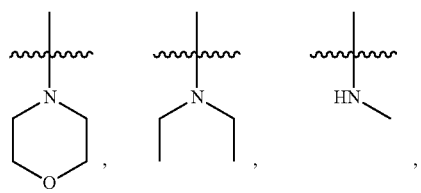

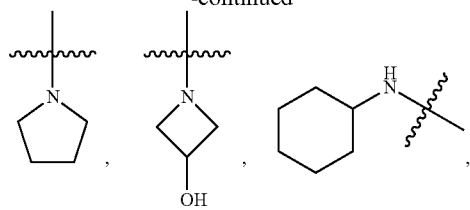

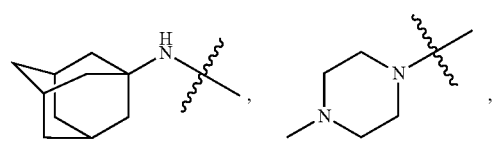

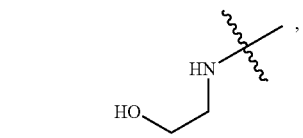

or —NR$^8$R$^2$, wherein R$^8$ and R$^9$ are independently selected from the group consisting of H, alkyl, aryl and heteroaryl; or R$^8$ and R$^9$ are optionally joined together to form a N-containing heterocycle with 1-3 heteroatoms.

2. The compound of claim 1, wherein $R^1$ is H.

3. The compound of claim 1, wherein $R^1$ is $R^4CO—$, and $R^4$ is alkyl, cycloalkyl, alkenyl, or aryl.

4. The compound of claim 1, wherein $R^1$ is $R^5NHCO—$ and $R^5$ is adamantyl.

5. The compound of claim 1, wherein $R^1$ is $R^6OCO—$, and $R^6$ is benzyl or substituted benzyl.

6. The compound of claim 1, wherein $R^1$ is $R^7SO_2—$ and $R^7$ is 4-fluorophenyl.

7. The compound of claim 1, wherein $R^2$ is alkyl.

8. The compound of claim 1, wherein $R^3$ is OH, —OMe, or allyloxy.

9. The compound of claim 1, wherein $R^3$ is

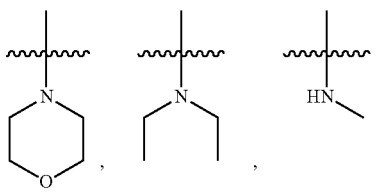

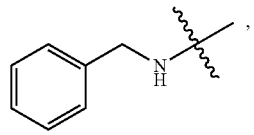

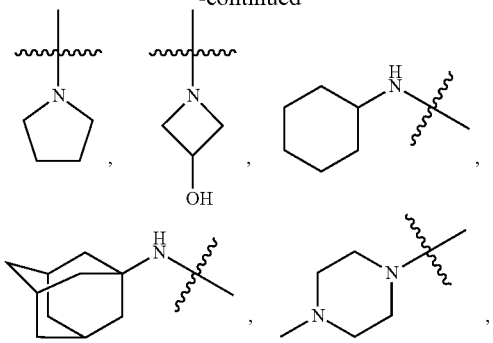
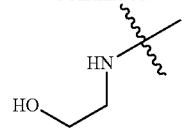
or, —NR⁸R⁹, wherein each of $R^8$ and $R^9$ is H.
10. The compound of claim 1, wherein the compound is selected from the group consisting of:
PW0165
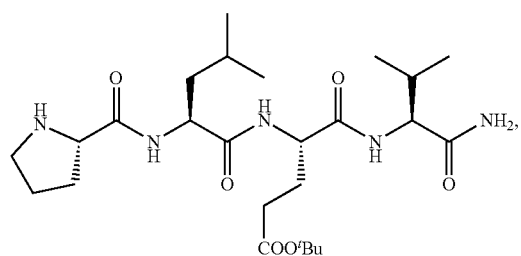
PW0184
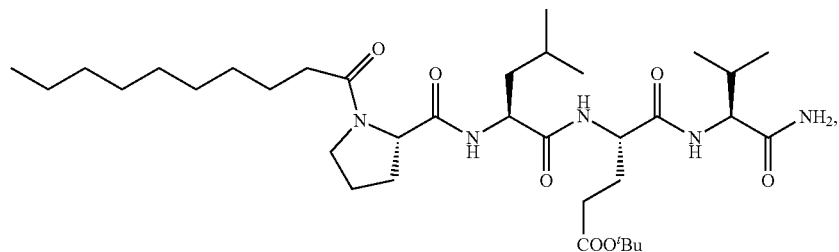
PW0169
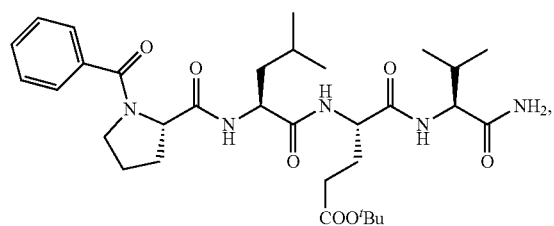
PW0183
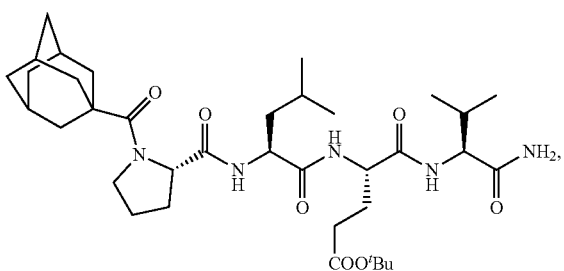
PW0185
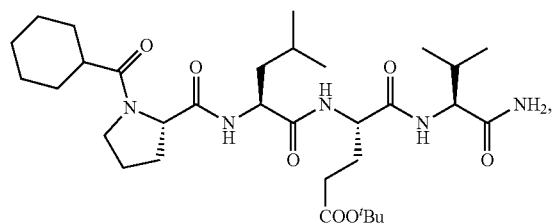
PW0192
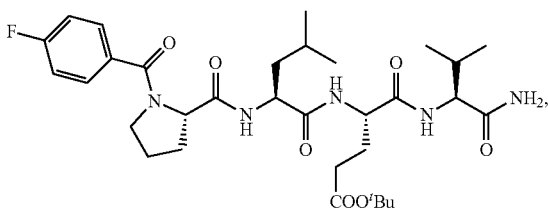

-continued
PW0173
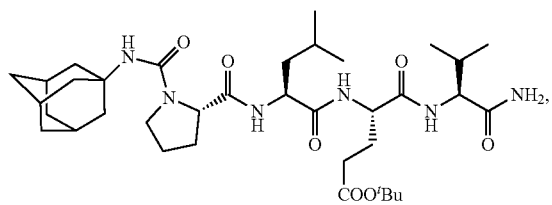
PW161
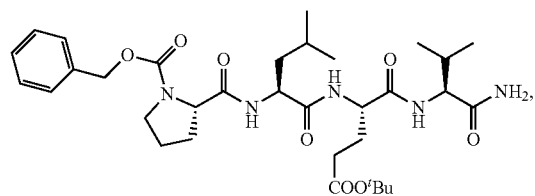
PW0164
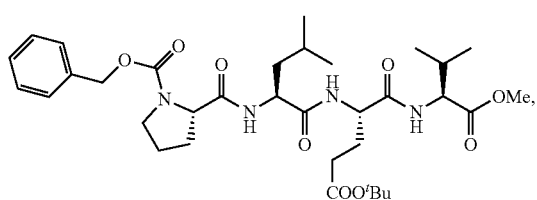
PW0197
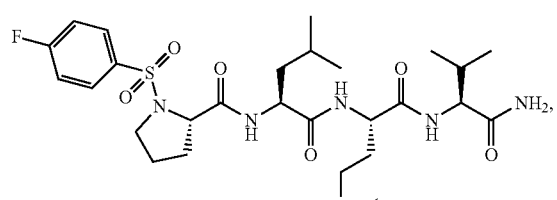
PW0564
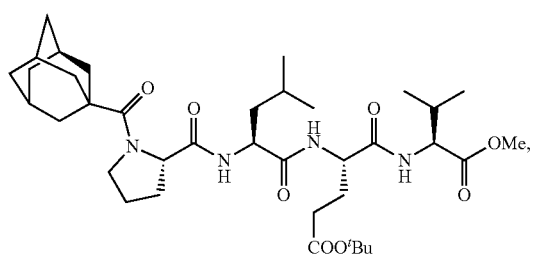
PW0565
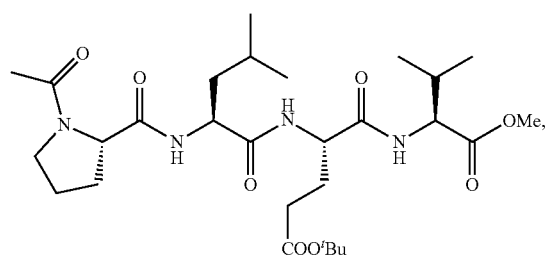
PW0576
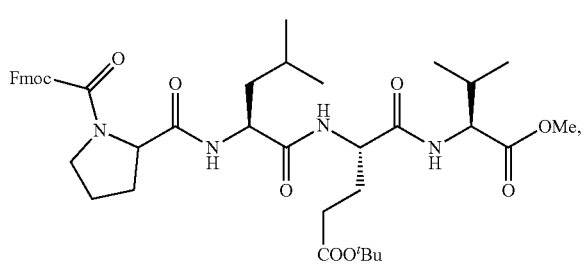
PW0531
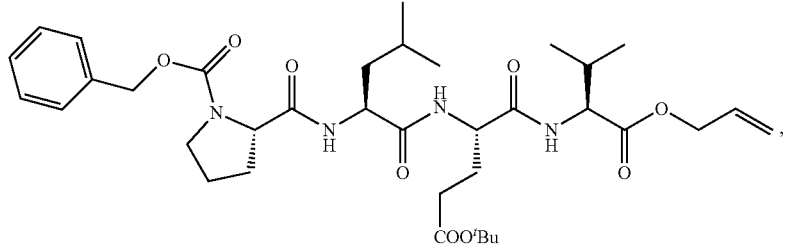
PW0533
PW0536
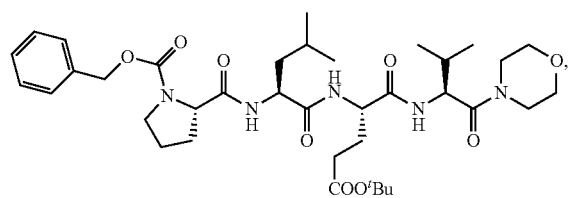

PW0540
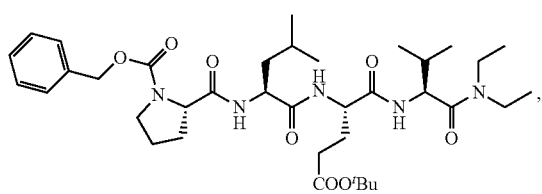
PW0541
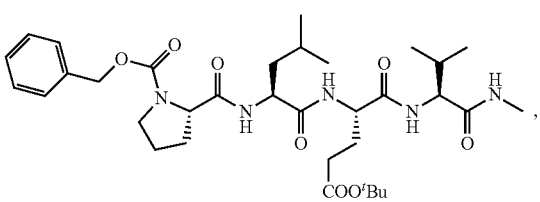
PW0542
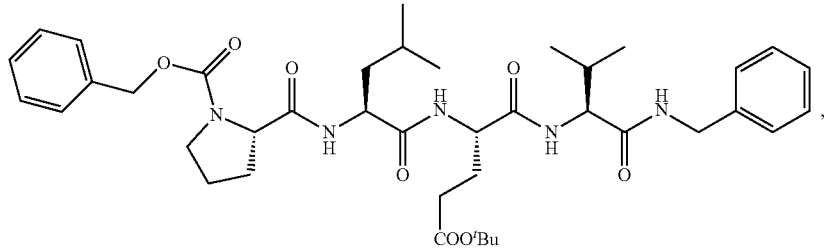
PW0543
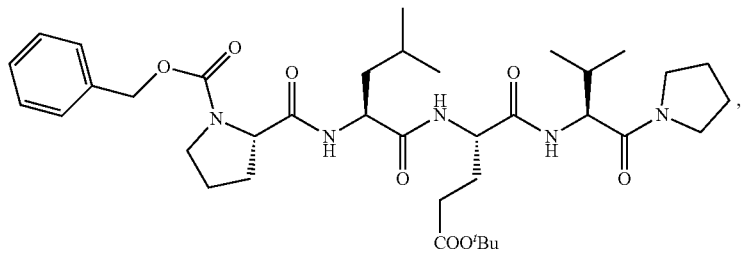
PW0544
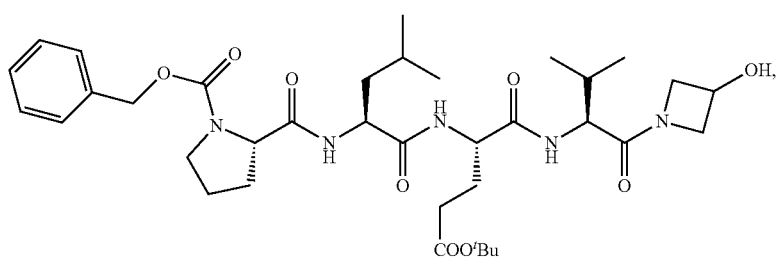
PW0545
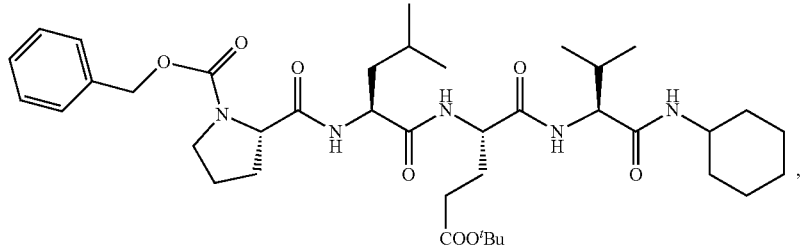
PW0547
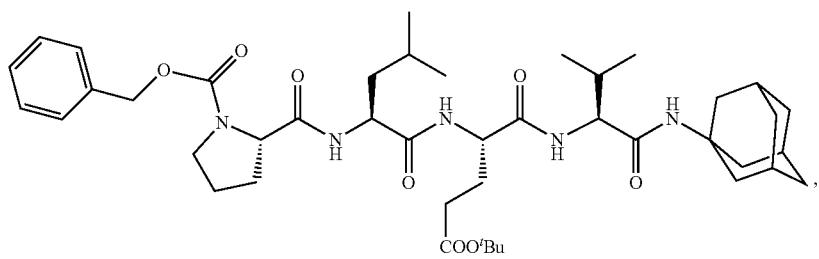

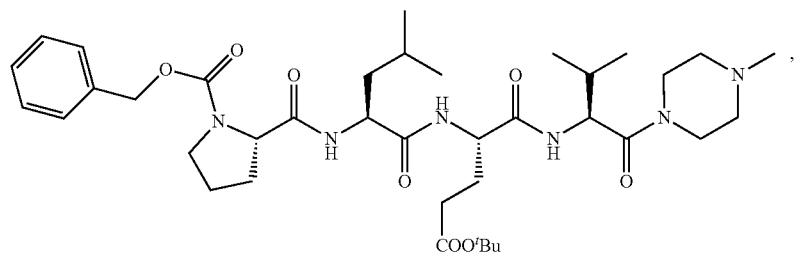
PW0559

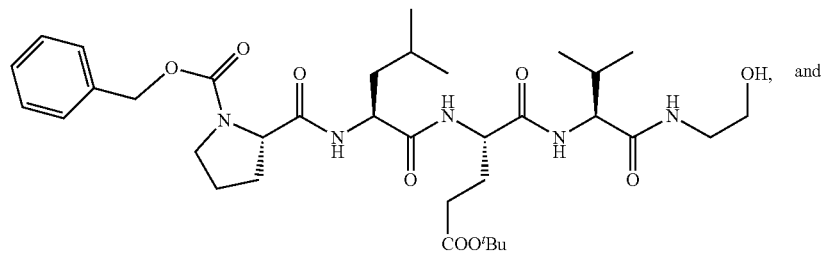
PW0561

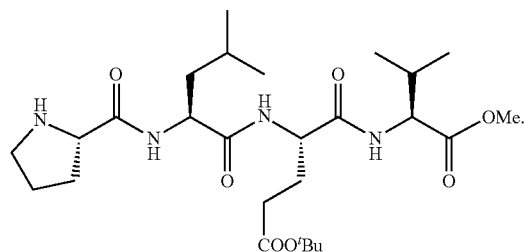
PW0539

11. The compound of claim 1, wherein $R^1$ is $R^6$OCO—, and wherein $R^6$ is selected from the group consisting of alkyl, cycloalkyl, alkenyl, aryl, heteroaryl, and benzyl, and $R^6$ is optionally substituted with one or more substituents selected from the group consisting of —OH, —CN, —NH$_2$, and halogen;

$R^2$ is alkyl; and $R^3$ is OH, —OMe, allyloxy,

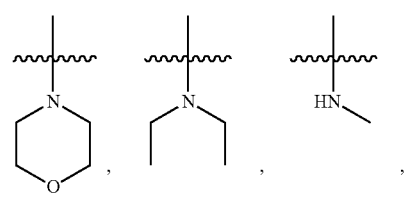

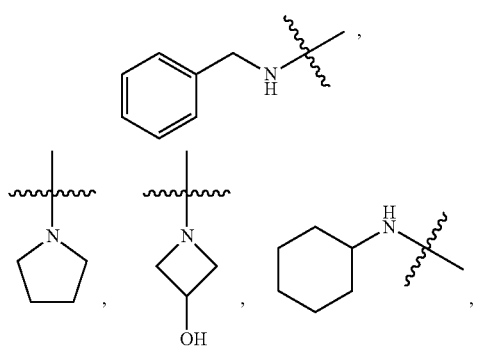

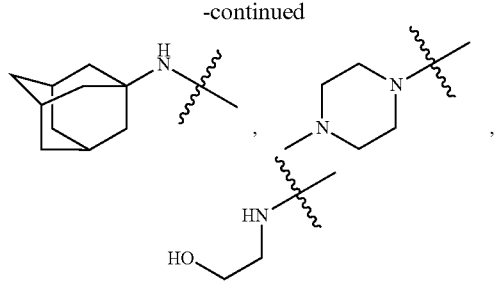

or —NR$^8$R$^9$, wherein each of $R^8$ and $R^9$ is H.

12. The compound of claim 11, wherein $R^2$ is t-butyl.
13. The compound of claim 11, wherein $R^6$ is benzyl or substituted benzyl.
14. The compound of claim 1, wherein $R^1$ is $R^4$CO— and $R^4$ is 4-fluorophenyl.
15. The compound of claim 1, wherein $R^4$, $R^5$, $R^6$ and $R^7$ are independently methyl or nC$_2$-C$_9$ alkyl.
16. The compound of claim 1, wherein $R^4$, $R^5$, $R^6$ and $R^7$ are n-nonyl.
17. The compound of claim 1, wherein $R^4$, $R^5$, $R^6$ and $R^7$ are 4-fluorophenyl.
18. A method of inhibiting fibroblast growth factor 13-1b (FGF13-1b) in cells, said method comprising contacting said cells with one or more compounds of claim 1 or pharmaceutically acceptable salt thereof.
19. A method of treating or alleviating pain by modulating FGF13-1b in a subject in need thereof, said method comprising administering one or more compounds of claim 1 or pharmaceutically acceptable salt thereof to said subject.

* * * * *